United States Patent [19]

Shephard et al.

[11] 4,041,055
[45] Aug. 9, 1977

[54] PROCESS FOR THE PREPARATION OF 17α-HYDROXYPROGESTERONES AND CORTICOIDS FROM ANDROSTENES

[75] Inventors: Kenneth Paul Shephard; Verlan H. Van Rheenen, both of Portage, Mich.

[73] Assignee: The Upjohn Company, Kalamazoo, Mich.

[21] Appl. No.: 632,671

[22] Filed: Nov. 17, 1975

[51] Int. Cl.$^2$ .................. C07J 5/00; C07J 7/00
[52] U.S. Cl. .................. 260/397.3; 260/397.4; 260/397.45; 260/397.47; 260/397.5; 260/239.5
[58] Field of Search ............ 260/397.3, 397.4, 397.45, 260/397.47, 397.5

[56] References Cited

U.S. PATENT DOCUMENTS 3,992,422  11/1976  Green .................. 260/397.45

FOREIGN PATENT DOCUMENTS 902,293  8/1962  United Kingdom ............ 260/397.45

Primary Examiner—Elbert L. Roberts
Attorney, Agent, or Firm—Bruce Stein

[57] ABSTRACT

This invention discloses a general process for the production of corticoids from androstenes. This invention provides an economically viable alternative synthesis of 17α-hydroxyprogesterones and the corticoids.

92 Claims, No Drawings

PROCESS FOR THE PREPARATION OF 17α-HYDROXYPROGESTERONES AND CORTICOIDS FROM ANDROSTENES

The corticoids are a particular type of steroid having the basic carbon skeletal formula

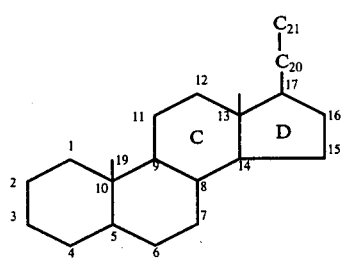

I which contains 21 carbon atoms in 4 rings, A thru D.

The A–D rings of the steroid nucleus being relatively planar will have some groups, at C-11 for instance, which are positioned above (β) the plane of cyclopentenophenanthrene nucleus and are designated by ◂R and others which are positioned below (α) the plane and are designated by ....R.

A well known example of the corticoids is hydrocortisone or cortisol which is represented by formula II

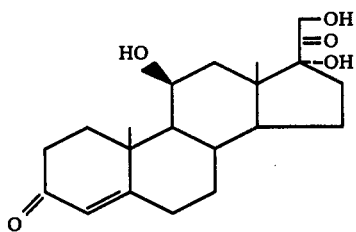

II

The pharmaceutical utility of the corticoids is well known to those skilled in the art. They are used for relief of inflammatory manifestations, endocrine disorders, adrenocortical insufficiency, rheumatic disorders, dermatologic diseases, allergic states, ophthalmic diseases, respiratory diseases, hematologic disorders, neoplastic diseases, edematous states, etc.

The corticoids are administered orally, topically or parenterally in dosages which are well known to those skilled in the art.

Sitosterol, a component of soybean oil and a readily available source of the steroid nucleus, can be converted to androstenedione by fermentation. See Chemical and Engineering News 53, 27 (1975). Androstenedione can be converted to ethisterone (17α-ethynyltestosterone). See H. H. Inhoffen and H. Köster, Ber. 723, 595 (1939). As used herein androstenedione means androst-4-ene-3,20-dione.

Ethisterone is well known to those skilled in the art. See The Merck Index, Merck and Co., Rahway, N.J., Eighth Edition, 1968, p. 428, and Steroids, Fieser and Fieser, Rienhold Publishing Co., New York, 1959, p. 557. $\Delta^{9(11)}$-Ethisterone is also known. See U.S. Pat. No. 3,441,559.

The present invention describes a general synthesis of converting androstenedione-type compounds into the corresponding 17α-hydroxyprogesterone-type compounds or the corticoid-type compounds. The chemical synthesis can be utilized for androstenedione-type compounds having various substituents. The androstenedione-type compounds may have a methyl substituent (α or β) at C-16; a fluorine, chlorine, bromine atom of hydroxyl group at C-9α; a methyl group or a fluorine atom at C-6α; a double bond between carbon atoms 1 and 2 and/or 9 and 11, and/or a hydroxyl group (α or β) or an oxygen atom at C-11. Androstenedione-type compounds are made by methods well known to those skilled in the art. Starting with an appropriately substituted androstenedione-type compound the process of the present invention will produce the correspondingly substituted 17α-hydroxyprogesterone-type compound or corticoid-type compound. Alternatively, one might start with an unsubstituted androstenedione-type compound, i.e. androstenedione, and produce the correspondingly unsubstituted corticoid-type compound, cortexolone (17α-hydroxydesoxycorticosterone). Following synthesis of the unsubstituted corticoid-type compound the desired substituents can then be added by methods well known to those skilled in the art. This permits great flexibility in using the process of the present invention to produce commercially desirable corticoid-type compounds. Since many of the corticoid-type compounds are of great medical and therapeutic significance this invention permits one to produce a desired corticoid-type compound with a short and economically advantageous synthesis.

When androstenedione or the androstenedione-type compounds are referred to they are deemed equivalent and meant to include the corresponding dehydroepiandrostenone (3α-hydroxy androst-5-ene-17-one) type compounds. The $\Delta^5$-3-hydroxy steriods containing 19 carbon atoms are deemed equivalent and are meant to be included with the androstenedione-type compounds because the $\Delta^4$-3-keto steriods of the androstenedione-type are readily prepared from the corresponding $\Delta^5$-3-hydroxy steriods by methods well known to those skilled in the art.

Disclosed is a process for the preparation of a steroid of the formula

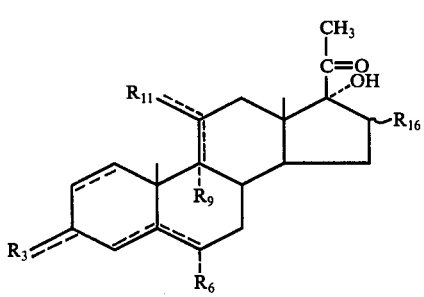

X which comprises starting with a steroidal propargyl alcohol of the formula

IV

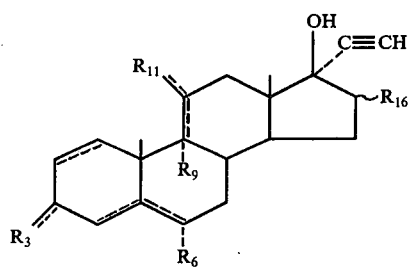

and subjecting the steroidal propargyl alcohol IV to the following reactions:

1. sulfenylating with a substituted sulfenylating agent of the formula $R_{17}$-S-M to form an allene sulfoxide of the formula

VI

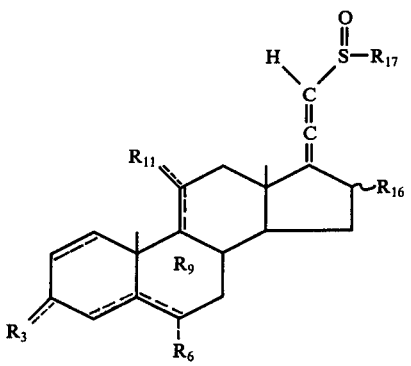

2. Micheal addition to the allene sulfoxide of step 1 with an alkoxide, mercaptide, or dialkylamine to form a sulfoxide of the formula

VII

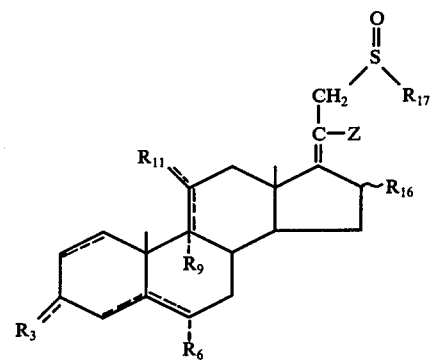

3. reacting the product of step 2 with a thiophile to form a compound of the formula

IX

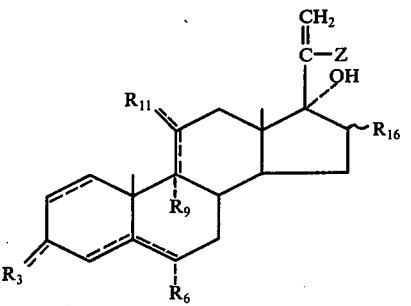

and 4. hydrolyzing the product of step 3 in the presence of an effective catalytic amount of an acid.

Further disclosed is a process for the preparation of a steroid of the formula

XII

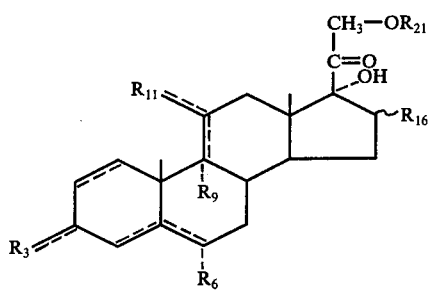

which comprises starting with the steroidal propargyl alcohol IV and subjecting the steroidal propargyl alcohol IV to the first 3 reactionsof the synthesis outlined above; and 4. adding a peracid to the product of step (3).

Further disclosed is an alternative process for the preparation of steriod XII which comprises starting with the steroidal propargyl alcohol IV and subjecting the steroidal propargyl alcohol IV to the first 3 reactions of the synthesis listed above; and 4. adding a halogen to the product of step (3) to produce a compound of the formula

XI

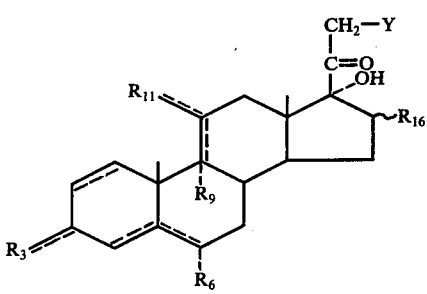

and 5. substituting an anion of the formula $OR_{21}$ for Y in the product of step (4).

Also disclosed is a process for the production of an allene sulfoxide of the formula VI 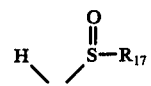

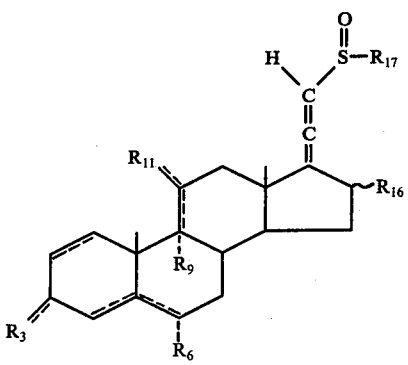

which comprises starting with a steroidal propargyl alcohol of the formula

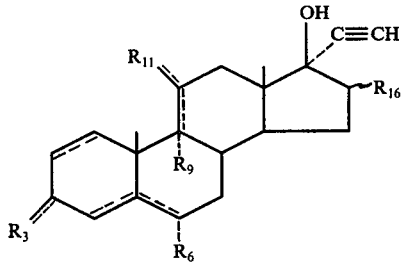
IV and sulfenylating the steroidal propargyl alcohol IV with a substituted sulfenylating agent of the formula $R_{17}$-S-M.

Also disclosed is a process for the preparation of a sulfoxide of the formula

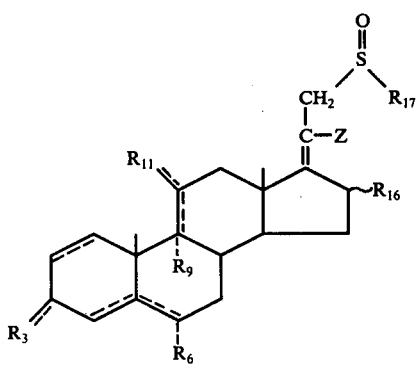
VII which comprises starting with an allene sulfoxide of the formula

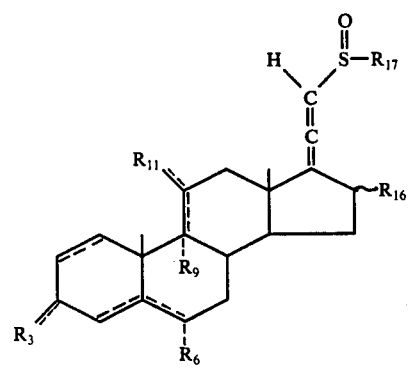
VI and subjecting the allene sulfoxide VI to Micheal addition with an alkoxide, mercaptide of dialkylamine.

Also disclosed is a process for the preparation of a 17α-hydroxy steriod of the formula

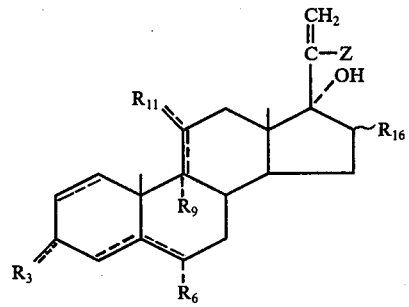
IX which comprises starting with a sulfoxide of the formula

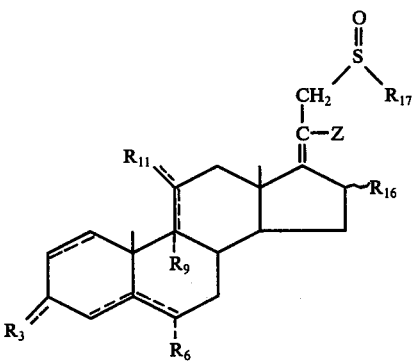
VII and reacting the formula VII compound with a thiophile.

Also disclosed is a process for the preparation of a steriod of the formula.

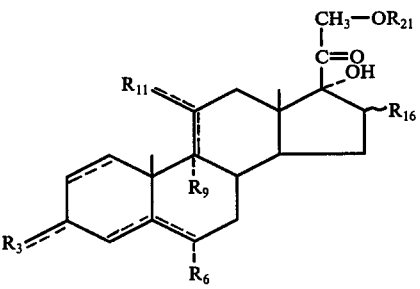
XII which comprises starting with a 17α-hydroxy steriod of the formula

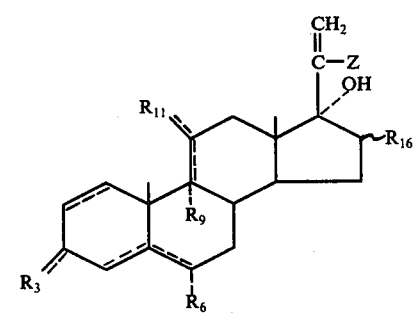
IX and adding a peracid.

Further disclosed is the formula VI allene sulfoxide, the formula VII sulfoxide, the formula IX 17α-hydroxy steriod and the formula XI 21-halo steriod. The structural formulas of the formula VI, VII, IX, and XI compounds are found in Charts A, B, and C.

With regards to the processes and compounds of this invention $R_3$, $R_6$, $R_9$, $R_{11}$, $R_{16}$, $R_{17}$, $R_{21}$, $\sim$, $===$ Z, Y, and M are defined below.

Charts A, B, and C more fully disclose the steps of the process of the present invention.

The formula III compound (Chart A) has an $R_{11}$ group at the C-11 position. $R_{11}$ is (H), (H,H), (H, αOH), (H,βOH), or (O). The symbol $===$ represents a single or double bond. This single or double bond can be found between carbon atoms 1 and 2, and carbon atoms 4 and 5 in ring A, between carbon atoms 9 and 11 in ring C and between $R_3$ and $C_3$ and between $R_{11}$ and $C_{11}$. When $R_{11}$ is (O) there is a double bond between the $R_{11}$ group, (O), and the C-11 carbon atom. The various combinations of $R_{11}$ and the double bonds in the C ring give the following substitution to the C ring at the C-11 position:

Chart A

III

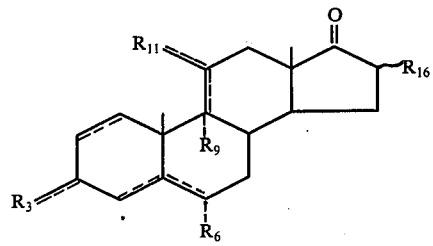

IV

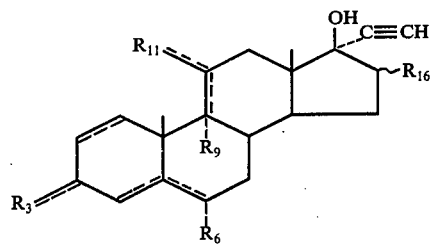

V

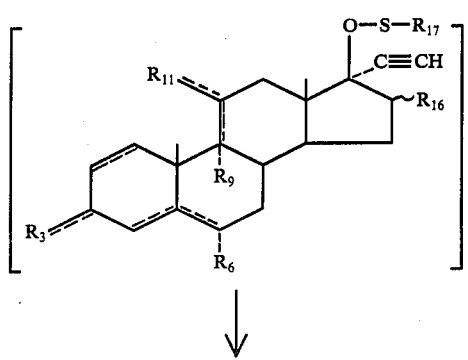

-continued
Chart A

VI

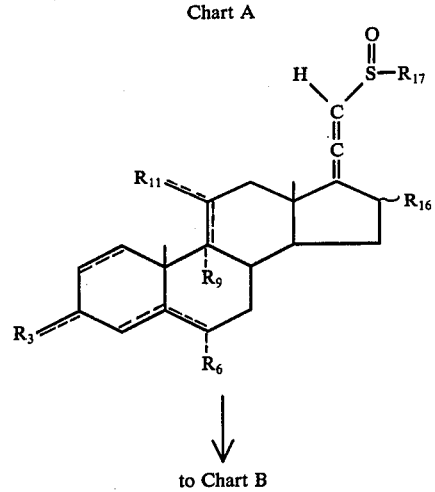

to Chart B

Chart B

VII

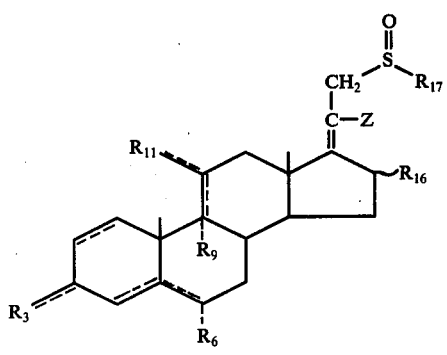

VIII

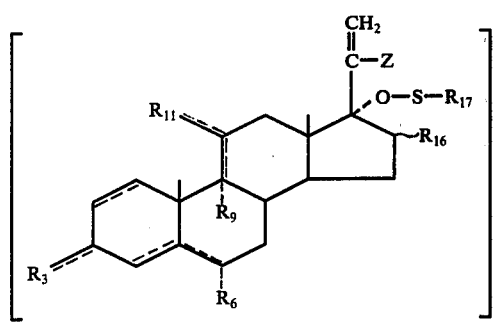

IX

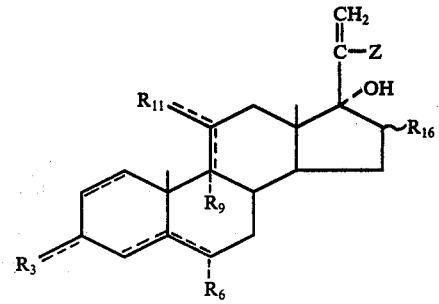

Chart C

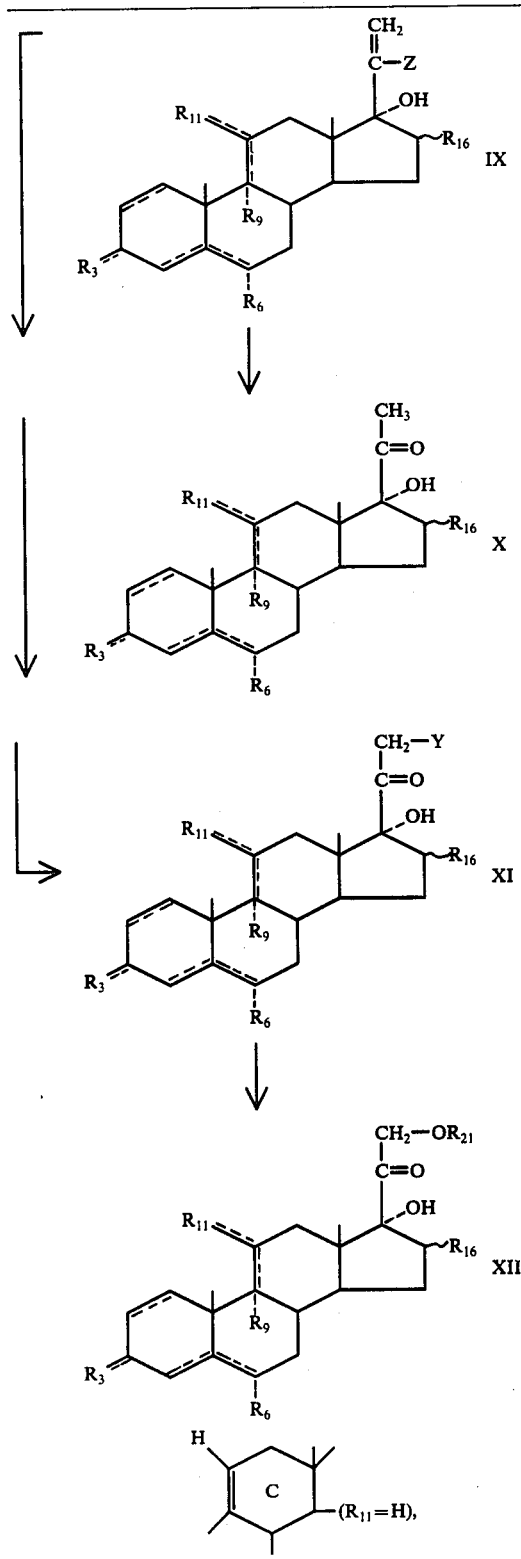

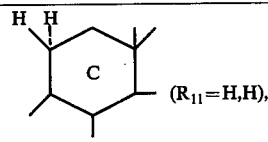
(R₁₁=H,H),

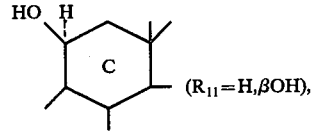
(R₁₁=H,βOH),

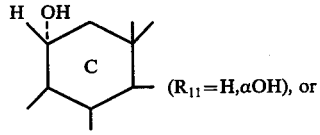
(R₁₁=H,αOH), or

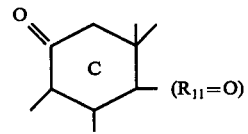
(R₁₁=O)

When C-11 is substituted, it is preferred that the substitution at C-11 for $R_{11}$ either be oxygen giving a 11-keto compound or a hydroxyl group in the beta position. The formula 111 compound has an $R_6$ group in the 6α position. $R_6$ is a hydrogen or fluorine atom or methyl group. The formula III compound has an $R_{16}$ group at the 16 position. $R_{16}$ is either a hydrogen atom or methyl group. The ~ incicates the $R_{16}$ group may be either the α or β position. The substitution at the 9 position is alpha and the substituent, $C_9$, is either a hydrogen, fluorine, chlorine, or bromine atom, or a hydroxyl group. It is preferred that when the position is substituted in steroids X and XII that the substituent be a fluorine atom. $R_3$ is an oxygen atom (O) or a hydroxyl group (HO) with the proviso that when $R_3$ is (O) there are double bonds between $C_3$ and $R_3$ and between $C_4$ and $C_5$, and when $R_3$ is (HO) there is a single bond between $C_3$ and $R_3$ with a double bond between $C_5$ and $C_6$.

The androstenedione-type compounds of formula III are readily converted to the propargyl alcohol-type compounds of formula IV by methods well known to those skilled in the art. For example, the formula 111 17-keto steriod can be protected in the A-ring as a ketal, enol ether or enamine. An acetylide salt such as LIC≡Ch is then added. Finally, the steriod protected in the A-ring is hydrolyzed to the formula IV alcohol. For enol ether protecting groups see H. H. Inhoffen and H. Köster, Ber. 723, 595 (1939). Alternatively, the formula III 17-keto steriod can be dissolved in an organic solvent such as THF and potassium t-butoxide and acetylene added. See Chem. Abs. 55, 27440 (1961).

The steroidal propargyl alcohol (formula IV) undergoes a sulfenation reaction with a substituted sulfenylating agent ($R_{17}$-S-M) to form an allene sulfoxide (formula VI). In the substituted sulfenylating agent M is a chlorine or bromine atom, phenylsulfone, phthalimide or imidazole group. It is preferred that M be a bromine or chlorine atom. It is more preferred that M be a chlorine atom. $R_{17}$ is alkyl of one thru 10 carbon atoms, trichloromethyl, phenyl or phenyl substituted with alkyl or one thru 4 carbon atoms, or substituted with one thru 3 nitro groups or substituted with one thru 3 trifluoromethyl groups, aralkyl of 7 thru 12 carbon atoms, phthalimide, $(R_{121})_2$-N where $R_{121}$ is alkyl of one thru 10 carbon atoms, phenyl, phenyl substituted with alkyl of one thru 4 carbon atoms, aralkyl of 7 thru 12 carbon atoms with the proviso that the two $R_{121}$ groups may be the same or different. Examples of alkyl of one thru 10 carbon atoms are methyl, ethyl, propyl, butyl, pentyl, hexyl, heptyl, octyl, nonyl, decyl, and isomeric forms thereof. Examples of phenyl substituted with alkyl of one thru 4 carbon atoms, with one thru 3 nitro groups, with one thru 3 trifluoromethyl groups are (o-, m-, or p-) tolyl, (o-, m-, or p-) ethylphenyl, p-tertbutylphenyl, 2,5 -dimethylphenyl, 2,6-dimethylphenyl, 2,4-dimethylphenyl, (2,3,4-, 2,3,5-, 2,3,6-, or 2,4,5-)-trimethylphenyl, (o-, m-, or p-)-nitrophenyl, 2,4-dinitrophenyl, 2,6-dinitrophenyl, 2,4,6-trinitrophenyl, (o-, m-, or p-) trifluoromethylphenyl. Examples of aralkyl of 7 thru 12 carbon atoms are benzyl, 2-phenylethyl, 1-phenylethyl, 2-phenylpropyl, 4-phenylbutyl, 3-phenylbutyl, 2-(1-naphthylethyl), and 1-)2-napthylmethyl). It is preferred that $R_{17}$ in the substituted sulfenylating agent be an aromatic group. It is more preferred that $R_{17}$ be phenyl or tolyl. It is most preferred that $R_{17}$ be phenyl. It is therefore preferred that the substituted sulfenylating agent be an aromatic sulfenyl chloride. It is more preferred that it be phenylsulfenyl chloride or tolylsulfenyl chloride. It is most preferred that it be phenylsulfenyl chloride.

The appropriately substituted sulfenylating agents are prepared by methods known to those skilled in the art. For example, sulfuryl chloride is added to a thiol previously dissolved in an organic solvent such as carbon tetrachloride. See Chem. Reviews, 39, 269 (1946) at page 279 and U.S. Pat. No. 2,929,820.

The sulfenation reaction is carried out in a non-polar aprotic solvent such as toluene, chloroform, ether, or methylene chloride. The reaction is carried out in the presence of at least an equal molar amount of a tertiary amine base, such as triethylamine or pyridine. Any excess base serves as additional solvent for the reaction. The reaction is preferably carried out at about $-70°$ but proceeds adequately in a temperature range of about $-80°$ to about 25°. The reaction is preferably carried out under an inert dry gas such as nitrogen, argon, or carbon dioxide. The substituted sulfenyl halide is added dropwise to the reaction mixture in a slight molar excess. If a much greater than molar amount is used, the reaction still proceeds, however, side reactions begin to occur. Following addition of the substituted sulfenylating agent to the reaction mixture the cooling bath is removed and the temperature is allowed to rise to about 20°, however, the temperature may be in the range of about $-30°$ to about 25°. The excess substituted sulfenylating agent is then quenched with an appropriate quenching agent such as water, cyclohexane, or various alcohols such as methanol and ethanol. The reaction is then washed with dilute acid such as 1N hydrochloric, sulfuric, phosphoric, acetic, etc. The concentration of the acid is not critical. The excess acid is removed with agents which are well known in the art such as sodium bicarbonate. The solvent is then removed and the product may be crystallized if it is so desired by methods well known in the art. However, the following reactions may be carried out on the reaction product without further purification.

The reaction of the steroidal propargyl alcohol (formula IV) with the substituted sulfenylating agent ($R_{17}$—S—M) to produce the allene sulfoxide (formula VI) is believed to proceed thru an intermediate (formula V). The chemical structure of the intermediate is believed to be that of the sulfenate ester shown as formula V in Chart A. The sulfenate ester intermediate cannot be isolated since it spontaneously undergoes a 2,3-sigmatropic rearrangement to form the allene sulfoxide of formula VI.

The formula VII (Chart B) sulfoxide is formed by Michael addition to the formula VI allene sulfoxide. In formula VII, Z is —O—$R_{20}$, —S—$R_{120}$ or —N—$(R_{120})_2$ where $R_{20}$ is alkyl of one thru 5 carbon atoms, phenyl or phenyl substituted with one thru 4 carbon atoms, aralkyl of 7 thru 12 carbon atoms and where $R_{120}$ is alkyl of one thru 5 carbon atoms. Examples of alkyl of one thru 5 carbon atoms, phenyl substituted with alkyl of one thru 4 carbon atoms and aralkyl of 7 thru 12 carbon atoms are found above. The Michael addition reaction may be carried out using alkoxides, mercaptides, or disubstituted amines. When an alkoxide is used for the reaction, the solvent is the corresponding alcohol. When the reactant is an alkoxide it is preferred that it be methoxide or ethoxide and it is especially preferred that it be methoxide. When the base is a dialkylamine it may serve as its own solvent. The Michael reaction is carried out peferably under an inert gas such as nitrogen. When the reaction is complete as measured by TLC, the reaction mixture is neutralized by methods well known to those skilled in the art. If isolation of the formula VII product is desired, it may be purified and crystallized according to work-up procedures well known to those skilled in the art.

The formula VII Michael addition product is in equilibrium with the formula VIII sulfenate ester. However, the equilibrium of this reaction lies far to the left. Therefore, most of the material present is in the form of the formula VII Michael addition product. The chemical structure of the sulfenate ester VIII is believed to be that shown in Chart B.

The formula VIII sulfenate ester is cleaved to form the formula IX enol derivative by thiophiles. However, some of the thiophiles, such as hydroxide, alkoxides, etc. produce many undesirable side reactions. Other thiophiles such as diethylamine and trimethylphosphite cleave the sulfenate ester and produce the enol derivative with fewer side reactions. Trimethylphosphite is the preferred thiophile. Trimethylphosphite is known as a thiophile, see D. A. Evans, and G. C. Andrews, Acct. of Chem. Res., 7, 147 (1974) at p. 150. When the formula VIII sulfenate ester is cleaved forming the formula IX enol derivative, the equilibrium between the formula VII sulfoxide and the formula VIII sulfenate ester is displaced to the right. The formula VIII sulfenate ester is not isolatable because the equilibrium of the reaction producing the formula VIII sulfenate ester lies far to the left and as it is formed from the formula VII sulfoxide, it is cleaved by the thiophile producing the formula IX enol derivative.

An alternative process to produce the formula IX enol derivative is to use the alkoxide present in the previous reaction (as the thiophile) which produced product VII and to heat this reaction mixture and/or continue the reaction for a longer period of time. This process is less desirable because it produces a lower yield and more numerous undesirable side reactions.

The thiophile (trimethylphosphite) is added to the reaction mixture containing steroid VI and it is refluxed until the reaction is complete as determined by TLC. This usually takes about 1 to 2 hours.

When the reaction is complete as measured by TLC, a small amount of aqueous base such as sodium hydroxide is added to insure that no acid is present. Acid hydrolysis of the formula IX enol derivative yields the formula X 17α-hydroxy progesterone type compound. The base is added so that if one wishes to continue the reaction sequence to produce a corticoid, acid hydrolysis of the formula IX enol derivative will not take place. The formula IX enol derivative is stable and may be isolated if no acid is present.

The allene sulfoxide VI produced consists of 2 diastereomers, isomeric at the sulfur atom. It is not necessary or even advantageous to attempt to separate the isomeric mixture since each isomer will react approximately equally well to produce the corresponding sulfoxide VII diastereomer. Each of the sulfoxide diastereomers is cleaved producing a single compound, the enol derivative IX, because upon cleavage the isomeric sulfur atom is lost. Formulas and chemical names of the allene sulfoxide VI, sulfoxide VII and sulfenate ester VIII are meant to include both isomers.

Chart C outlines the production of the formula X 17α-hydroxyprogesterone type compounds and the formula XII corticoid type compounds from the formula IX enol derivative.

The formula IX enol derivative may be readily converted to the formula X 17α-hydroxyprogesterone type compound by aqueous acid hydrolysis. A catalytic amount of an acid such as p-TSA may be conveniently used for this purpose. Most organic solvents such as THF, chloroform, ethanol, and acetone are suitable for the reaction. It is preferred that the organic solvent be water-miscible. The temperature at which the reaction is carried out is not critical. The reaction is followed to completion by TLC and usually takes about 15 min. to about 1 hr.

L. Horner and V. Binder in Liebigs, Ann. Chem. 757, 33 (1972) reported the addition of a sulfenyl chloride to simple aliphatic and monocyclic propargyl alcohols to give allene sulfoxides and the subsequent conversion of the allene sulfoxides to α-hydroxyketones. The present invention uses similar chemistry to convert 17-keto steroids into biologically active 17α-hydroxyprogesterones and cortical steroids. Even though some of the steps of the present invention are similar to those reported by Horner and Binder the fact that the present invention yields the desired products stereoselectively and in good yield is unexpected and surprising for a number of reasons.

Horner and Binder used as their starting material simple aliphatic and unsubstituted monocyclic propargyl alcohols. The starting material of the present invention differs in two respects. The reactants of the present invention are not monocyclic but rather tetracyclic and in addition are substituted with various functionality. It is well known that certain positions of the steroid nucleus are unreactive due to steric hinderance. This is particularly true of substituents at $C_{11}$ and $C_{17}$ because of steric hinderance of the angular methyl groups $C_{18}$ and $C_{19}$. For example, acetylation of transdihydroandrosterone gives the 3-acetate at room temperature, but it requires 115° for 20 hr. to affect acetylation of the secondary alcohol at the $C_{17}$ position. See L. Rudzick and K. Hoffman, Helv., 20, 1280 (1937). The 17β-alcohol group in ethisterone and $\Delta^{9(11)}$-ethisterone is even more hindered than in transdihydroandrosterone because it is a tertiary alcohol group. It was therefore surprising and unexpected that the bulky sulfenylating agent, phenylsulfenyl chloride would react with the hindered tertiay 17β-alcohol in ethisterone and $\Delta^{9(11)}$-ethisterone. A number of other reactions which proceed well in unhindered aliphatic cases do not work when applied to the sterically hindered C-17 position in a steroid. For example the Wittig reaction with $(C_6H_5)_3P=CHCOOC_2H_5$ and the Horner reaction with $(C_2H_5O)_2POCH_2COOC_2H_5$ do not proceed with 17-keto steroids presumably because of steric hinderance, although these reactions are commonplace with unhindered aldehydes and ketones. See A. K. Bose and D. T. Dahill, Tet. Lett., 959 (1963) and J. Org. Chem., 30, 505 (1964). It is therefore, surprising and quite unexpected that the reactions reported by Horner and Binder for simple unsubstituted aliphatic and monocyclic propargyl alcohols would proceed to any significant degree on a steroidal reactant.

It is also surprising and unexpected that the reaction proceeded with such a high degree of selectivity in view of the other functionality in the ethisterone and $\Delta^{9(11)}$-ethisterone molecule. The reactant propargly alcohols used by Horner and Binder had no functionality other than that at the reactive site. In view of the fact that phenylsulfenyl chloride is known to react with olefins (P. T. Landsbury, J. C. S. Chem. Comm., 21 (1974)), it was most surprising and unexpected that the double bonds at $C_4$ in ethisterone, and $C_4$ and $C_{9(11)}$ in $\Delta^{9(11)}$-ethisterone did not interfere with the phenylsulfenyl chloride reaction.

The propargly alcohol reactants for Horner and Binder were symmetrical. The reactant propargyl alcohols of the present invention are asymmetrical. An essential feature of the chemistry of the present invention is the inversion of the 17β-hydroxy group in the reactant to the 17α-hydroxy group present in both the 17α-hydroxyprogesterone and the cortical steroids products. This critical stereochemical inversion cannot be predicted from Horner and Binder's article since all their substracts were symmetrical. Therefore, the high stereospecificity for the 17α-configuration was surprising and unexpected. Further, this result was more surprising and unexpected in view of the high yields of product obtained.

The present invention discloses a process for synthesis of steroidal cortical side chain which has oxygen functions at $C_{17}$ specifically in the α position as well as oxygen functions at $C_{20}$ and $C_{21}$. None of these oxygen functions are present in the starting propargyl alcohol. Horner and Binder did not disclose how to make the gross structure of the cortical side chain even on non-steroidal reactants and therefore, clearly does not suggest a process for synthesis of the cortical side chain on a steroid nucleus. It is, therefore, not obvious from the article of Horner, and Binder that the steroidal cortical side chain could be synthesized by the process disclosed by the present invention. It is even less obvious that the steroidal cortical side chain could be synthesized on a steroidal nucleus.

The formula IX enol derivative may be converted directly to the formula XII corticoid by addition of a peracid. In formula XII, $R_{21}$ is a hydrogen atom or alkyl carboxylate of 2 thru 6 carbon atoms or aromatic carboxylate of 7 thru 12 carbon atoms. Examples of alkyl carboxylate of 2 thru 6 carbon atoms are acetyl, propionyl, butyryl, valeryl, hexanoyl, and isomers thereof. Examples of aromatic carboxylate of 7 thru 12 carbon atoms are benzoyl, phenylacetyl, phenylpropionyl, phenylbutyryl, phenylvaleryl, phenylhexanoyl, and isomers thereof. Most peracids are suitable and the corresponding ester of the peracid is obtained as a corticoid product. For example, if the peracid is peracetic acid the 21-acetate of the corticoid is the product. It is preferred that the peracid be peracetic acid. The reaction is carried out in an organic solvent or mixed solvents such as benzene, ethyl acetate, acetone, or chloroform. A base such as sodium acetate is added to the organic solvent so as to neutralize the sulfuric acid present in the commercially produced peracids that are used in this process. The reaction may be carried out at a temperature of −30° to 25°. It is preferable that the reaction temperature be about 0° to about 5°. It is preferred that the reaction is carried out under an inert dry gas such as nitrogen. When the reaction is complete as measured by TLC, it is quenched with an agent such as sodium sulfite or sodium hydrosulfite. The reaction can then be worked up by means well known to those skilled in the art.

An alternative synthesis of the formula XII corticoid from the formula IX enol derivative is thru the formula XI 21-halo-17-hydroxyprogesterone analog. In formula XI, Y is a chlorine, bromine, or iodine atom. It is preferred that Y is a bromine atom. The halogen is added to a solution of the formula IX enol derivative in an organic solvent containing an amine base. Examples of the organic solvent are benzene, chloroform, toluene, and ethyl acetate. An example of the amine base, is triethylamine and it should be present in at least molar quantities. It is preferable that the halogen be present in quantities approximately the same as that of the amine base and more preferably just slightly less than the amine base. The time of the reaction is not critical and it is followed to completion by TLC. The formula XI 21-halo-ketone is formed by acid hydrolysis. The nature of the acid is not critical and most acids such as sulfuric, phosphoric, or P-TSA are suitable for this reaction.

The formula XI 21-halo-17α-hydroxyprogesterone analog is converted to the formula XII corticoid by substituting an anion such as acetate for the 21-halogen atom. The anion must contain an oxygen atom negatively charged and can be hydroxide, alkyl carboxylate or aromatic carboxylate. The different anions used will produce the correspondingly different esters at the 21-position of the corticoid. If the anion is acetate the formula XII corticoid product produced will be the 21-acetate ester. If the anion is benzoate the formula XII product will be the 21-benzoate ester. It is preferred that the anion be acetate. If Y is chlorine or bromine it is preferred to use iodide in the acylate displacement. Although not necessary it does facilitate the reaction. The reaction may be carried out in various organic solvents. It is preferred that the organic solvent be polar such as acetone or DMF (dimethylformamide), however, organic solvents such as ethyl acetate are suitable.

All temperatures are in degrees centigrade.
TLC refers to thin-layer chromatography.
Saline refers to an aqueous saturated sodium chloride solution.
SSB refers to Skellysolve β, an isomeric mixture of hexanes.
THF refers to tetrahydrofuran.
NMR refers to nuclear magnetic resonance.
NMR spectra were recorded on a Varian A-60 spectrophotometer with tetramethylsilane (TMS) as an internal standard and the chemical shifts are reported in ppm (δ) relative to TMS, TMS=0.000 δ.

Melting points were determined on a Thomas Hoover Capillary melting point apparatus.
UV refers to ultraviolet.
UV spectra were determined on a Beckman DV Model 2400 Spectrophotometer.
p-TSA refers to p-toluenesulfonic acid.
Optical rotation was determined on a Perkin-Elmer Polarimeter.
DMF refers to dimethylformamide.
Androstenedione refers to androst-4-ene-3,20-dione.
The invention can be more fully understood by the following examples.

PREPARATION 1

Ethisterone (17α-Ethynyltestosterone)

A. 3-Ethyl enol ether of androstenedione

Androstenedione (229.12 g.), triethylorthoformate (157.64 ml.) and absolute ethanol (280 ml.) are stirred for 5 min. Pyridine hydrochloride (0.40 g.) is added and the mixture stirred at 40° under nitrogen for 4 hr. until the reaction is complete as measured by TLC. Triethylamine (1.5 ml.) is added, the mixture is cooled to 0°–5° and the crystalline solids filtered. The solids are washed on the filter with ethanol previously cooled to 0° containing a small amount of triethylamine. The solids are dried under vacuum yielding 214.70 g. of 3-ethyl enol ether of androstenedione.

B. 17α-Ethynyltestosterone-3-ethyl enol ether

The steroid product of step A above is dissolved in 1300 ml. of THF. This solution is added over a 35 min. period to 144 g. of lithium acetylide ethylene diamine which is kept under nitrogen. The reaction is stirred under nitrogen for 4.5 hr. until complete as measured by TLC in 80–20 SSB-ethyl acetate. Deionized water (684 ml.) is added during 15 min. The mixture is transferred to a 5 l. separatory funnel. The aqueous layer is then separated and extracted with 300 ml. of ethyl acetate. The THF solution and the ethyl acetate extract are combined and washed with 2 portions of 684 ml. of saturated ammonium chloride solution and one portion of 342 ml. of saturated ammonium chloride solution. The steriod-THF-ethyl acetate solution is then washed with 684 ml. of deionized water followed by a washing with 684 ml. of saline. The washed organic solution is then dried over magnesium sulfate, filtered, and concentrated under vacuum on a steam bath to a solid.

C. Ethisterone (17α-Ethynyltestosterone)

Methanol (900 ml.) is added to the crude solids of step B above. The mixture is stirred under nitrogen at 35°–40°. Water (244 ml.) containing 12.6 g. of pyridine hydrochloride is added. The mixture is stirred on the steam bath keeping the temperture at 40°–45° for 3½hr. until the reaction is complete as measured by TLC. The reaction mixture is cooled on an ice bath to 0°–5° and filtered. The filtered solids are washed with three 150-ml. portions of deionized water and vacuum dried at 50°–60° to yield 189 g. of the title compound.

PREPARATION 2

Phenylsulfenyl chloride

Carbon tetrachloride (120 ml.) is deoxygenated by bubbling nitrogen through the solvent for 10 to 15 min. Pyridine (0.6 ml.) is added to the carbon tetrachloride and the resulting solution is warmed to 60°. Thiophenol (32.16 g., 30.0 ml.) is added to the above solution dropwise. Sulfuryl chloride (53.18 g., 31.9 ml.) is added dropwise to the above mixture while maintaining the temperature at 60°. The reaction mixture is then stirred at 60° for 30 min. During the addition of the surfuryl chloride the color of the reaction mixture turns from yellow to orange and finally to a deep red. The reaction mixture is concentrated under reduced pressure to a red oil, filtered and then distilled under vacuum to give 33.77 g. (0.2335 mole) of phenylsulfenyl chloride b.p. 38° (0.8 mm).

EXAMPLE 1

21-Phenylsulfinylpregna-4,17(20),20-triene-3-one (Formula VI: $R_3$ is (O), $R_{11}$ is (H,H), $R_6$, $R_9$, and $R_{16}$ are hydrogen, and === between $C_1$ and $C_2$ in the A ring is a single bond).

Refer to Chart A. A slurry of Ethisterone (70.0 g., Preparation 1), methylene chloride (2100 ml.) and triethylamine (90.0 ml.) is cooled to −70° under nitrogen with stirring. To the slurry is added dropwise a solution of freshly distilled phenylsulfenyl chloride (36.0 g., Preparation 2) in methylene chloride (83 ml.) over a period of 105 min. The reaction mixture is allowed to warm-up to −30° over about 2 hr. with stirring. The reaction mixture is held at −30° for 45 min. with stirring. Methanol (20 ml.) is added and 2-3 min. later cyclohexene (5 ml.) is added. Deionized water (200 ml.) is added to the reaction mixture which is then warmed to 5°. The methylene chloride layer is separated from the aqueous layer and washed with 1N hydrochloric acid (400 ml.), a 2.5 percent sodium bicarbonate solution (100 ml.) and deionized water (200 ml.). The methylene chloride solution is dried over anhydrous magnesium sulfate. The dried methylene chloride solution is concentrated at atmospheric pressure on a steam bath to a volume of about 125 ml. Acetone (200 ml.) is added, and the solution is concentrated to a small volume. Acetone (200 ml.) is added and the mixture is concentrated to a volume of about 200 ml. This slurry is cooled to about 0° to 5° and filtered. The solids are washed with some acetone-Skelly B (40-60) previously cooled to 0°, then with Skelly B (50 ml.) and dried under vacuum to give 78.29 g. of the title compound. m.p. 169°-171.5°, $[\alpha]_D$ (CHCl$_3$) +214.2°, UV (methanol) $\lambda_{max.}$ = 233 m$\mu$ ($\epsilon$ = 31,843). A second crop of crystals (6.0 gm.) is also obtained.

Following the procedure of Example 1, but substituting the propargyl alcohols of Column A for Ethisterone there are obtained the corresponding allene sulfoxides of Column B.

| Example | Reactant (Column A) | Allene Sulfoxide (Column B) |
|---|---|---|
| 2 | 6α-Methylethisterone | 6α-methyl-21-phenylsulfinyl-pregna-4,17(20),20-triene-3-one |
| 3 | 11β-Hydroxyethisterone | 11β-Hydroxy-21-phenylsulfinyl-pregna-4,17(20),20-triene-3-one |
| 4 | 11β-Hydroxy-6α-methylethisterone | 11β-Hydroxy-6α-methyl-21-phenylsulfinylpregna-4,17-(20)20-triene-3-one |

The reactants for Examples 2 thru 4 in column A are either known to those skilled in the art or can be readily prepared from known compounds by methods well known to those skilled in the art.

EXAMPLE 5

20-Methoxy-21-phenylsulfinylpregna-4,17(20)-diene-3-one (Formula VII; $R_3$ is (O), $R_{11}$ is (H,H), $R_6$, $R_9$, and $R_{16}$ are hydrogen, $R_{17}$ is phenyl, Z is O—$R_{20}$, $R_{20}$ is methyl, and === between $C_1$ and $C_2$ in the A ring is a single bond.

Refer to Chart B. A mixture of 21-phenylsulfinylpregna-4,17(20),20-triene-3-one (60.0 g., Example 1), methanol (760 ml.) and sodium methoxide (11.4 g.) is stirred at about 34°-35° under nitrogen for 6 hr. Glacial acetic acid (12 ml.), is added to the reaction mixture followed by pyridine (4 ml.). The title compound may be isolated if one desires or may be reacted further as shown in Chart B without isolation.

Following the procedure of Example 5 but substituting the allene sulfoxides of Examples 2 thru 4 (column B) for 21-phenylsulfinylpregna-4,17(20),20-triene-3-one there are obtained the corresponding sulfoxides of Column C.

| Example | REACTANT (Allene sulfoxide from Example) | SULFOXIDE (Column C) |
|---|---|---|
| 6 | 2 | 20-Methoxy-6α-methyl-21-phenyl-sulfinylpregna-4,17(20)-diene-3-one |
| 7 | 3 | 11β-Hydroxy-20-methoxy-21-phenylsulfinylpregna-4,17(20)-diene-3-one |
| 8 | 4 | 11β-Hydroxy-20-methoxy-6α-methyl-21-phenylsulfinylpregna-4,17(20)-diene-3-one |

EXAMPLE 9

17α-Hydroxy-20-methoxypregna-4,20-diene-3-one (Formula IX: $R_3$ is (H,H), $R_6$, $R_9$, and $R_{16}$ are hydrogen, Z is O—$R_{20}$, $R_{20}$ is methyl, and === between $C_1$ and $C_2$ in the A ring is a single bond.

Refer to Chart B. Freshly distilled trimethylphosphite (22 ml.) is added to the reaction product of Example 5 which is then refluxed for 1.5 hr. The reaction mixture is concentrated under reduced pressure to a volume of 260 ml. A solution of 1N aqueous sodium hydroxide (8 ml.) in deionized water (1200 ml.) is added slowly to the slurry. The resulting slurry is cooled to about 0°-5° and filtered. The solids are washed with SSB (300 ml.) and finally with SSB (300 ml.) containing pyridine (2 ml.). The solids are dried under vacuum at 65° to give 47.193 g. of title compound. NMR (CDCl$_3$) = 0.65, 1.18, 3.54, 5.71, 4.08, and 4.25 δ.

Following the procedure of Example 9, but substituting the sulfoxides of Examples 6 thru 8 (Column C) for 20-methoxy-21-phenylsulfinylpregna-4,17(20)-diene-3-one there are obtained the corresponding 17α-hydroxy steroids of column D.

| Example | REACTANT (Sulfoxide from Example) | 17α-Hydroxy Steroid (Column D) |
|---|---|---|
| 10 | 6 | 17α-Hydroxy-20-methoxy-6α-methyl-pregna-4,20-diene-3-one |
| 11 | 7 | 11β,17α-Dihydroxy-20-methoxypregna-4,20-diene-3-one |
| 12 | 8 | 11β,17α-Dihydroxy-20-methoxy-6α-methylpregna-4,20-diene-3-one |

EXAMPLE 13

17α-Hydroxyprogesterone (Formula X: $R_3$ is (O), $R_{11}$ is (H,H), $R_6$, $R_9$, and $R_{16}$ are hydrogen, and $\equiv\equiv\equiv$ between $C_1$ and $C_2$ in the A ring is a single bond.)

Refer to Chart C. A mixture of 17α-hydroxy-20-methoxy-pregna-4,20-diene-3-one (1.0 g., Example 9), methanol (5 ml.), deionized water (1 ml.), and p-TSA (0.1 g.) is stirred at about 25° for 30 min. The reaction mixture is filtered and the solids are washed with deionized water. The solids are dried under vacuum at about 65° to give 0.85 g. of the title compound. NMR (CDCL$_3$) = 0.72, 1.19, 2.25, and 5.73 δ which is identical to an authentic sample. TLC (1.5 = methanol-98.5% chloroform) $R_f$ = 0.50.

Following the procedure of Examples 1, 5, 9, and 13 but substituting the reactant of Column E below for ethisterone the corresponding product of column F are obtained.

| Example | Reactant (Column E) | Product (Column F) |
|---|---|---|
| 14 | 9α-fluoro-11β-hydroxy-ethisterone | flurogestone (9α-fluoro-11β,17α-dihydroxypregna-4-ene-3,20-dione) |
| 15 | 9α-fluoro-6α-methyl-11β-hydroxy-Δ$^1$-ethisterone | fluorometholone (9α-fluoro-11β,17α-dihydroxy-6α-methyl-pregna-1,4-diene-3,20-dione) |
| 16 | 6α-methyl-ethisterone | medroxyprogesterone (11β,17α-dihydroxy-6α-methylpregna-4-ene-3,20-dione) |

The reactants for examples 14 thru 16 in column E above are either known to those skilled in the art or can be readily prepared from known compounds by methods well known to those skilled in the art. See Preparation 1.

EXAMPLE 17

17α,21-Dihydroxypregna-4-ene-3,20-dione 21-acetate (Formula XIII: $R_3$ is (O), $R_{11}$ is (H,H), $R_6$, $R_9$, and $R_{16}$ are hydrogen, $R_{21}$ is acetate, and $\equiv\equiv\equiv$ between $C_1$ are $C_2$ in the A ring is a single bond.

Refer to Chart C. A mixture of 17α-hydroxy-20-methoxypregna-4,20-diene-3-one (3.0 g., Example 9), methylene chloride (45 ml.), ethyl acetate (75 ml.), and anhydrous sodium acetate (3.0 g.) is cooled to 0°–5° under nitrogen with stirring. To this mixture is added 2.26 ml. of 40 percent peracetic acid. The slurry is stirred at 0°–5° for 2 hr. The reaction is quenched by the addition of aqueous sodium thiosulfate solution. The layers are separated and the organic layer is washed with a solution of sodium bicarbonate (1.0 g.) in deionized water (30 ml.). The organic layer is then washed with two 30 ml. portions of deionized water and one 30 ml. portion of saline. The organic layer is then dried over anhydrous magnesium sulfate. The dried solution is concentrated to a thick crystalline slurry under reduced pressure. Methanol is added and the resulting slurry is concentrated to a low volume under reduced pressure and filtered. The solids are washed with a little methanol previously cooled to about 0° and then dried under vacuum at 65° to give 2.309 g. of the title compound. m.p. 229°–235.5°; NMR (CDCl$_3$) = 0.71, 1.19, 4.98, and 5.73 δ and is identical to an authentic sample; UV (methanol) $\lambda_{max.}$ = 242 mμ (ε = 17,055); [α]$_D$ acetone + 107.8°.

EXAMPLE 18

21-Bromo-17α-hydroxypregna-4-ene-3,20-dione (Formula XI: $R_3$ is (O), $R_{11}$ is (H,H), $R_6$, $R_9$, and $R_{16}$ are hydrogen, Y is bromine, and $\equiv\equiv\equiv$ between $C_1$ and $C_2$ in the A ring is a single bond.)

Refer to Chart C. A solution of 17α-hydroxy-20-methoxypregna-4,20-diene-3-one (47.55 g., Example 9) and pyridine (12.656 g., 12.94 ml.) in methylene chloride (470 ml.) is cooled to 0°–5° under nitrogen with stirring. To this solution is added dropwise a solution of bromine (25.57 g., 8.25 ml.) in methylene chloride (100 ml.) After stirring for 30 min. at 0°–5° the reaction mixture is transferred to a separatory funnel and washed with 1N aqueous hydrochloric acid (70 ml.). The organic layer is then washed with a solution of sodium sulfite (4 g.) in deionized water (100 ml.) and finally with deionized water (100 ml.). The organic solution is dried over anhydrous magnesium sulfate and evaporated to dryness yielding the title compound. NMR (CDCl$_3$) = 0.72, 1.18, 4.3 and 5.73 δ.

Following the procedure of Example 18 but substituting the 17α-hydroxy steroids of Examples 10 thru 12 (Column D) for 17α-hydroxy-20-methoxypregna-4,20-diene-3-one there are obtained the corresponding 21-halo steroids of Column G.

| Ex. | REACTANT (17α-hydroxy steroid of Example) | 21-Halo-steroid (Column G) |
|---|---|---|
| 19 | 10 | 21-Bromo-17α-hydroxy-6α-methyl-pregna-4-ene-3,20-dione |
| 20 | 11 | 21-Bromo-11β,17α-dihydroxypregna-4-ene-3,20-dione |
| 21 | 12 | 21-Bromo-11β,17α-dihydroxy-6α-methylpregna-4-ene-3,20-dione |

EXAMPLE 22

17α,21-Dihydroxypregna-4-ene-3,20-dione 21-acetate (Formula XII: $R_3$ is (O), $R_{11}$ is (H,H), $R_6$, $R_9$, and $R_{16}$ are hydrogen, $R_{21}$ is acetate, and $\equiv\equiv\equiv$ between $C_1$ and $C_2$ in the A ring is a single bond.

Refer to Chart C. 21-Bromo-17α-hydroxypregna-4-ene-3,20-dione (Example 18) is heated at reflux with acetone (670 ml.), potassium acetate (81.9 g.), glacial acetic acid (25.3 ml.) and potassium iodide (43.3 g.) for 2 hr. The slurry is then slowly diluted with deionized water (1130 ml.). The acetone is removed under reduced pressure. The resulting slurry is cooled to 0°–5°, washed with deionized water, and the solids dried under vacuum at 70° to give 52.604 g. of the title compound.

Following the procedure of Examples 1, 5, 9, and 17 or Examples 1, 5, 9, 18, and 22 but substituting the reactants of column H for ethisterone the corresponding products of column I are obtained.

| Example | Reactant (Column H) | Product (Column I) |
|---|---|---|
| 23 | 9α-chloro-11β-hydroxy-16β methyl-Δ$^1$-ethisterone | beclomethasone (9α-chloro-11β,17α,21-trihydroxy-16β-methylpregna-1,4-diene-3,20-dione) |
| 24 | 9α-fluoro-11β-hydroxy-16β-methyl-Δ$^1$-ethisterone | betamethasone (9α-fluoro-11β,17α,21-trihydroxy-16β-methylpregna-1,4-diene-3,20-dione) |

-continued

| Example | Reactant (Column H) | Product (Column I) |
|---|---|---|
| 25 | $\Delta^1$-11-keto-ethisterone | cortisone (17α,21-dihydroxypregna-4-ene-3,11,20-trione) |
| 26 | 9α-fluoro-11β-hydroxy-16α-methyl-$\Delta^1$-ethisterone | dexamethasone (9α-fluoro-11β,17α,21-trihydroxy-16α-methylpregna-1,4-diene-3,20-dione) |
| 27 | 6α,9α-difluoro-11β-hydroxy-16β-methyl-$\Delta^1$-ethisterone | difluorasone (6α,9α-difluoro-11β,17α,21-trihydroxy-16β-methylpregna-1,4-diene-3,20-dione 17,21-diacetate) |
| 28 | 9α-fluoro-11β-hydroxy-$\Delta^1$-ethisterone | fludrocortisone (9α-fluoro-11β,17α,21-trihydroxypregna-4-ene-3,20-dione) |
| 29 | 6α,9α-difluoro-11β-hydroxy-16α-methyl-$\Delta^1$-ethisterone | flumethasone (6α,9α-difluoro-11β,17α,21-trihydroxy-16α-methylpregna-1,4-diene-3,20-dione) |
| 30 | 6α-fluoro-11β-hydroxy-$\Delta^1$-ethisterone | fluprednisolone (6α-fluoro-11β,17α,21-trihydroxypregna-1,4-diene-3,20-dione) |
| 31 | 11β-hydroxyethisterone | hydrocortisone (11β,17α,21-trihydroxypregna-4-ene-3,20-dione) |
| 32 | 16β-methyl-$\Delta^1$-11-keto-ethisterone | meprednisone (17α,21-dihydroxy-16β-methyl-pregna-1,4-diene-3,11,20-trione) |
| 33 | 6α-methyl-11β-hydroxy-$\Delta^1$-ethisterone | methylprednisolone (11β,17α,21-trihydroxy-6α-methylpregna-1,4-diene-3,20-dione) |
| 34 | 6α-fluoro-11β-hydroxy-16α-methyl-$\Delta^1$-ethisterone | paramethasone (6α-fluoro-11β,17α,21-trihydroxy-16α-methylpregna-1,4-diene-3,20-dione) |
| 35 | 11β-hydroxy-$\Delta^1$-ethisterone | prednisolone (11β,17α,21-trihydroxypregna-1,4-diene-3,20-dione) |
| 36 | $\Delta^1$-11-keto-ethisterone | prednisone (17α,21-dihydroxypregna-1,4-diene-3,11,20-trione) |

The reactants for Examples 23 thru 36 in column H above are either known to those skilled in the art or can be readily prepared from known compounds by methods well known to those skilled in the art.

EXAMPLE 37

21-Phenylsulfinylpregna-4,9)11),17(20),20-tetraene-3-one (Formula VI; $R_3$ is (O), $R_{11}$ is (H), $R_6$ and $R_{16}$ are hydrogen, and === between $C_1$ and $C_2$ in the A ring is a single bond).

Refer to Chart A. $\Delta^{9(11)}$-ethisterone (20.0 g., See U.S. Pat. No. 3,441,559 is added to a mixture of methylene chloride (600 ml.) and triethylamine (25 ml.). The mixture is cooled to −70°. Freshly distilled phenylsulfenyl chloride (Preparation 2, 10.2 g.) in methylene chloride (25 ml.) is added dropwise to the reaction mixture under nitrogen. The reaction mixture is permitted to warm to about −25° over a period of 1.0 hr. After the reaction mixture is at about −25° methanol (5 ml.), cyclohexene (1 ml.), and deionized water (56 ml.) is added sequentially. The reaction mixture is warmed to about 4°. The reaction mixture is worked up by washing the methylene chloride layer with 1N hydrochloric acid (100 ml.), sodium bicarbonate (2.5 percent), and finally with deionized water. The methylene chloride is then dried and the mixture concentrated to yield a solid. The title compound is obtained by crystallization from acetone, m.p. 165°–167°. NMR (CDCl$_3$) = 0.89, 1.33, 5.53, 5.75, 6.17 and 7.58 δ. A second crop of crystals is also obtained.

Following the procedure of Example 37, but substituting the propargyl alcohols of Column J for $\Delta^{9(11)}$-ethisterone there are obtained the corresponding allene sulfoxides of Column K.

| Example | Reactant (Column J) | Allene Sulfoxide (Column K) |
|---|---|---|
| 38 | $\Delta^{1,9(11)}$-ethisterone | 21-Phenylsulfinylpregna-1,4,9(11),17(20),20-pentaene-3-one |
| 39 | 6α-methyl-$\Delta^{9(11)}$-ethisterone | 6α-Methyl-21-phenylsulfinyl-pregna-4,9(11),17(20),20-tetraene-3-one |
| 40 | 6α-Methyl-$\Delta^{1,9(11)}$-ethisterone | 6α-Methyl-21-phenylsulfinyl-pregna-1,4,9(11),17(20),20-pentaene-3-one |
| 41 | 6α-Fluoro-$\Delta^{9(11)}$-ethisterone | 6α-Fluoro-21-phenylsulfinyl-pregna-4,9(11),17(20),20-tetrane-3-one |
| 42 | 6α-Fluoro-$\Delta^{1,9(11)}$-ethisterone | 6α-Fluoro-21-phenylsulfinyl-pregna-1,4,9(11),17(20),20-pentaene-3-one |
| 43 | 16α-Methyl-$\Delta^{9(11)}$-ethisterone | 16α-Methyl-21-phenylsulfinyl-pregna-4,9(11),17(20),20-tetraene-3-one |

The reactants for Examples 38 thru 43 in Column J are either known to those skilled in the art or can be readily prepared from known compounds by methods well known to those skilled in the art.

EXAMPLE 44

20-Methoxy-21-phenylsulfinylpregna-4,9(11),17(20)-triene-3-one (Formula VII; $R_3$ is (O), $R_{11}$ is (H), $R_6$ and $R_{16}$ are hydrogen, $R_{17}$ is phenyl, Z is O—$R_{20}$, $R_{20}$ is methyl, and === between $C_1$ and $C_2$ in the A ring is a single bond).

Refer to Chart B. 21-phenylsulfinylpregna-4,9(11),17(20),20-tetraene-3-one (Example 37, 7.0 g.) is added to methanol (50 ml.). Sodium methoxide (1.0 g.) is added slowly to the mixture. The reaction mixture is stirred at about 25° utilizing some cooling until the reaction is complete as measured by TLC. Upon completion of the reaction a 10 percent phosphate buffer (pH = 6.8) is added dropwise followed by the addition of deionized water (50 ml.). The precipitate is filtered, thoroughly washed with deionized water and dried under vacuum to yield 7.3 g. of the title compound. m.p. 156°–160°. NMR (CDCl$_3$) = 0.47, 1.30, 3.54, 3.78, 5.5, 5.73, and 7.52 δ.

Following the procedure of Example 44, but substituting the allene sulfoxides of Examples 38 thru 43 (Column K) for 21-phenylsulfinylpregna-4,9(11),17(20),20-tetraene-3-one there are obtained the corresponding sulfoxides of Column L.

| Example | REACTANT (Allene sulfoxide from Example) | SULFOXIDE (Column L) |
|---|---|---|
| 45 | 38 | 20-Methoxy-21-phenylsulfinyl-pregna-1,4,9(11),17(20)-tetraene-3-one |
| 46 | 39 | 20-Methoxy-6α-methyl-21-phenyl-sulfinylpregna-4,9(11),17(20)- |

-continued

| Example | REACTANT (Allene sulfoxide from Example) | SULFOXIDE (Column L) |
|---|---|---|
| 47 | 40 | 20-Methoxy-6α-methyl-21-phenyl-sulfinylpregna-1,4,9(11),17(20)-tetraene-3-one |
| 48 | 41 | 6α-Fluoro-20-methoxy-21-phenyl-sulfinylpregna-4,9(11),17(20)-triene-3-one |
| 49 | 42 | 6α-Fluoro-20-methoxy-21-phenyl-sulfinylpregna-1,4,9(11),17(20)-tetraene-3-one |
| 50 | 43 | 20-Methoxy-16α-methyl-21-phenyl-sulfinylpregna-4,9(11),17(20)-triene-3-one |

EXAMPLE 51

17α-Hydroxy-20-methoxypregna-4,9(11),20-triene-3-one (Formula IX: $R_3$ is (O), $R_{11}$ is (H), $R_6$ and $R_{16}$ are hydrogen, and ≡≡≡ between $C_1$ and $C_2$ in the A ring is a single bond).

Refer to Chart B. 20-Methoxy-21-phenylsulfinylpregna-4,9(11),17(20)-triene-3-one (2.0 g., Example 44) is stirred in methanol (25 ml.). Freshly distilled trimethylphosphite (0.61 ml.) is added and the reaction brought to reflux under nitrogen. After 1.5 hr. of reflux TLC showed a trace of the starting compound remaining. The reaction was refluxed an additional hour. The reaction is then concentrated to about one-half volume under vacuum during which time the title compound crystallizes out in well formed crystals. To this slurry is added a 5 percent sodium bicarbonate solution (10 ml.), the slurry is filtered, washed with a dilute sodium bicarbonate-methanol mixture (1:1), air dried, washed with SSB (10 ml.) and dried under vacuum to yield 1.4 g. of the title compound, m.p. 170°–175°.

Following the procedure of Example 51, but substituting the sulfoxides of Examples 45 thru 50 (Column L) for 20-methoxy-21-phenylsulfinylpregna-4,9(11),17(20)-triene-3-one there are obtained the corresponding 17α-hydroxy-steroids of column M.

| Example | REACTANT (Sulfoxide from Example) | 17α-Hydroxy Steroid (Column M) |
|---|---|---|
| 52 | 45 | 17α-Hydroxy-20-methoxypregna-1,4,9(11),20-tetraene-3-one |
| 53 | 46 | 17α-Hydroxy-20-methoxy-6α-methyl-pregna-4,9(11),20-triene-3-one |
| 54 | 47 | 17α-Hydroxy-20-methoxy-6α-methyl-pregna-1,4,9(11),20-tetraene-3-one |
| 55 | 48 | 6α-Fluoro-17α-hydroxy-20-methoxy-pregna-4,9(11),20-triene-3-one |
| 56 | 49 | 6α-Fluoro-17α-hydroxy-20-methoxy-pregna-1,4,9(11),20-tetraene-3-one |
| 57 | 50 | 17α-Hydroxy-20-methoxy-16α-methylpregna-4,9(11),20-triene-3-one |

EXAMPLE 58

$\Delta^{9(11)}$-17α-Hydroxyprogesterone (Formula X: $R_3$ is (O), $R_{11}$ is (H), $R_6$ and $R_{16}$ are hydrogen and ≡≡≡ between $C_1$ and $C_2$ in the A ring is a single bond).

Refer to Chart C. A mixture of 17α-hydroxy-20-methoxy-pregna-4,9(11),20-triene-3-one (0.26 g., Example 51), deionized water (0.3 ml.) and p-TSA (0.030 g.) is stirred at about 25° for 1 hr. Deionized water (about 2 ml.) is added, the white solid filtered, thoroughly washed with deionized water and vacuum dried to yield the title compound (0.24 g.). m.p. = 206°–211° NMR (CDCl$_3$) = 0.69, 1.36, 2.27, 3.23, 5.59, and 5.77 δ.

EXAMPLE 59

21-Bromo-17α-hydroxypregna-4,9(11)-diene-3,20-dione (Formula XI: $R_3$ is (O), $R_{11}$ is (H), $R_6$ and $R_{16}$ are hydrogen, Y is bromine and ≡≡≡ between $C_1$ and $C_2$ in the A ring is a single bond).

Refer to Chart C. A solution of 17α-hydroxy-20-methoxy-pregna-4,9(11),20-triene-3-one (0.475 g., Example 51), methylene chloride (5 ml.) and pyridine (0.13 ml.) is cooled to 0°–5° under nitrogen with stirring. Bromine (0.256 g., 0.082 ml.) dissolved in methylene chloride (1 ml.) is added dropwise to the cooled solution. The reaction mixture is stirred until completion as measured by TLC (about 1 hr.). The reaction mixture is washed with 1N aqueous hydrochloric acid. The excess bromine is quenched with an aqueous sodium sulfite solution. The organic phase is then separated, washed with deionized water, dried over sodium sulfate, and concentrated to a foam. The foam is added to acetone (6 ml.) yielding the title compound in crystalline form.

Following the procedure of Example 59, but substituting the 17α-hydroxy steroids of Examples 52 thru 57 (Column M) for 17α-hydroxy-20-methoxypregna-4,9(11),20-triene-3-one there are obtained the corresponding 21-halo steroids of Column N.

| Example | REACTANT (17α-hydroxy steroid of Example) | 21-Halo-steroid (Column N) |
|---|---|---|
| 60 | 52 | 21-Bromo-17α-hydroxypregna-1,4,9(11)-triene-3,20-dione |
| 61 | 53 | 21-Bromo-17α-hydroxy-6α-methyl-pregna-4,9(11)-diene-3,20-dione |
| 62 | 54 | 21-Bromo-17α-hydroxy-6α-methyl-pregna-1,4,9(11)-triene-3,20-dione |
| 63 | 55 | 21-Bromo-6α-fluoro-17α-hydroxy-pregna-4,9(11)-diene-3,20-dione |
| 64 | 56 | 21-Bromo-6α-fluoro-17α-hydroxy-pregna-1,4,9(11)-triene-3,20-dione |
| 65 | 57 | 21-Bromo-17α-hydroxy-16α-methyl-pregna-4,9(11)-diene-3,20-dione |

EXAMPLE 66

17α,21-Dihydroxypregna-4,9(11)-diene-3,20-dione 21-acetate (Formula XII: $R_3$ is (O), $R_{11}$ is (H), $R_6$ and $R_{16}$ are hydrogen, $R_{21}$ is acetate and ≡≡≡ between $C_1$ and $C_2$ in the A ring is a single bond).

Refer to Chart C. 21-Bromo-17α-hydroxypregna-4,9(11)-diene-3,20-dione (Example 59) is mixed with acetone (6 ml.) to give a slurry. Potassium acetate (0.8 g.), acetic acid (0.2 ml.) and potassium iodide (0.1 g.) are added to the slurry and refluxed for 2 hr. Additional acetone is added and the mixture refluxed for 1 hr. Deionized water (10 ml.) is added, the mixture cooled, filtered, washed with deionized water and dried under vacuum yielding crystals. The title compound is obtained upon recrystallization from ethyl acetate. m.p. = 230°–232° NMR (CDCl$_3$) = 0.67, 1.37, 2.17, 3.25, 5.02, 5.61 and 5.77 δ.

We claim:

1. A process for the preparation of a steriod of the formula

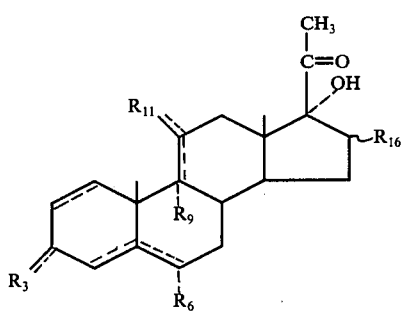

X where $R_3$ is an oxygen atom (O) or a hydroxyl group (HO) with the proviso that when $R_3$ is (O) there are double bonds between $C_3$ and $R_3$ and between $C_4$ and $C_5$, and when $R_3$ is (HO) there is a single bond between $C_3$ and $R_3$ a double bond between $C_5$ and $C_6$; where $R_6$ is a hydrogen or fluorine atom or methyl group; where $R_9$ is a hydrogen, fluorine, chlorine, or bromine atom, or hydroxyl group; where $R_{11}$ is (H), (H,H), (H,$\alpha$OH), (H,$\beta$OH) or (O); where $R_{16}$ is a hydrogen atom or methyl group; where $\sim$ indicates the attachment of the $R_{16}$ group in the alpha or beta configuration; and where $\equiv\equiv\equiv$ is a single or double bond which comprises starting with a steroidal propargyl alcohol of the formula

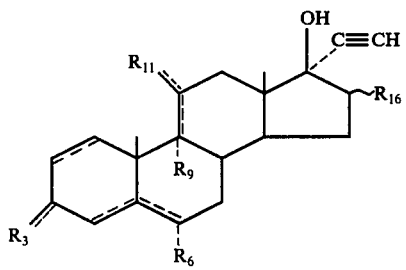

IV where $R_3$, $R_6$, $R_9$, $R_{11}$, $R_{16}$, $\sim$, and $\equiv\equiv\equiv$ are defined above and subjecting the steroidal propargyl alcohol IV to the following reactions:
1. sulfenylating with a substituted sulfenylating agent of the formula $R_{17}$-S-M; where M is a chlorine or bromine atom, phenylsulfone, phthalimide or imidazole group; where $R_{17}$ is alkyl of one thru 10 carbon atoms, trichloromethyl, phenyl or phenyl substituted with one thru 3 nitro groups or substituted with one thru 3 trifluoromethyl groups, aralkyl of 7 thru 12 carbon atoms, phthalimide, $(R_{121})_2$-N where $R_{121}$ is alkyl of one thru 10 carbon atoms, phenyl, phenyl substituted with alkyl of one thru 4 carbon atoms, aralkyl of 7 thru 12 carbon atoms with the proviso that the two $R_{121}$ groups may be the same or different, to form an allene sulfoxide of the formula

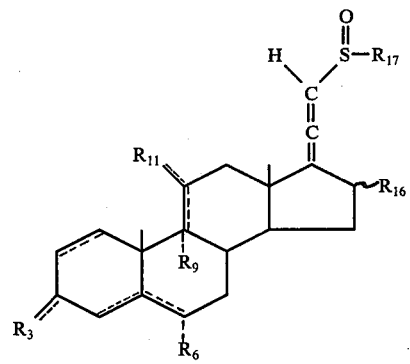

VI where $R_3$, $R_6$, $R_9$, $R_{11}$, $R_{16}$, $R_{17}$, $\sim$, and $\equiv\equiv\equiv$ are defined above;
2. Michael addition to the allene sulfoxide of step (1) with an alkoxide, mercaptide or dialkyl amine to form a sulfoxide of the formula

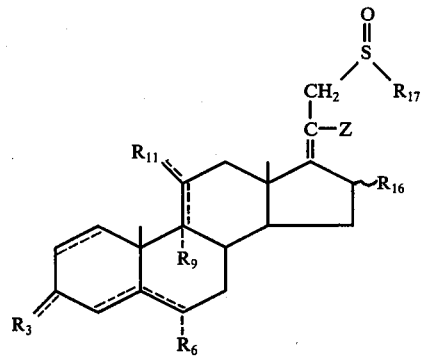

VII where $R_3$, $R_6$, $R_9$, $R_{11}$, $R_{16}$, $R_{17}$, $\sim$, and $\equiv\equiv\equiv$ are defined above and where Z is -O-$R_{20}$, -S-$R_{120}$ or -N-$(R_{120})_2$ where $R_{20}$ is alkyl of one thru 5 carbon atoms, phenyl or phenyl substituted with one thru 4 carbon atoms, or alkyl of 7 thru 12 carbon atoms, and where $R_{120}$ is alkyl of one thru 5 carbon atoms;
3. reacting the product of step (2) with a thiophile selected from the group consisting of trimethylphosphite and diethylamine to form a compound of the formula

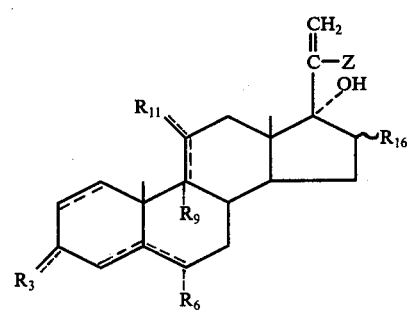

IX where $R_3$, $R_6$, $R_9$, $R_{11}$, $R_{16}$, $\sim$, $\equiv\equiv\equiv$, and Z are defined above; and
4. hydrolyzing the product of step (3) in the presence of an effective catalytic amount of an acid.
2. A process according to claim 1, where the substituted sulfenylating agent is an aromatic sulfenyl chloride, and where the Michael addition is with an alkoxide.

3. A process according to claim 2, where the aromatic sulfenyl chloride is phenylsulfenyl chloride or tolysulfenyl chloride and where the alkoxide is methoxide or ethoxide.

4. A process according to claim 3, where the aromatic sulfenyl chloride is phenylsulfenyl chloride, where the alkoxide is methoxide and the thiophile is trimethylphosphite.

5. A process according to claim 4 where the steroid of formula X is flurogestone (9α-fluoro-11β,17α-dihydroxypregna-4-ene-3,20-dione).

6. A process according to claim 4, where the steroid of formula X is fluorormethonone (9α-fluoro-11β,17α-dihydroxy-6α-methylpregna-1,4-diene-3,20-dione).

7. A process according to claim 4, where the steroid of formula X is medroxyprogesterone (11β,17α-dihydroxy-6α-methylpregna-4-ene-3,20-dione).

8. A process for the preparation of a steroid of the formula

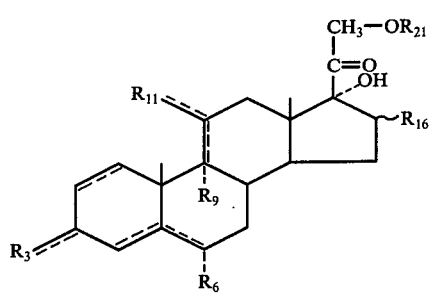

XII where $R_{21}$ a hydrogen atom or alkyl carboxylate or 2 thru 6 carbon atoms, or aromatic carboxylate of 7 thru 12 carbon atoms; which comprises starting with a steroidal propargyl alcohol of the formula

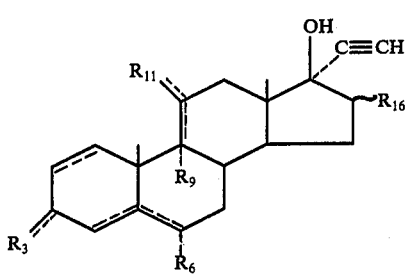

IV and subjecting the steroidal propargyl alcohol IV to the following reactions:

1 sulfenylating with a substituted sulfenylating agent of the formula $R_{17}$-S-M, to form an allene sulfoxide of the formula

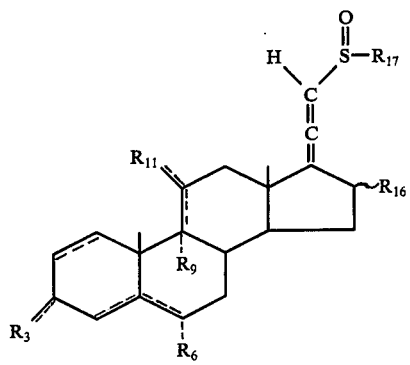

VI

2. Michael addition to the allene sulfoxide of step (1) with an alkoxide, mercaptide or dialkyl amine to form a sulfoxide of the formula

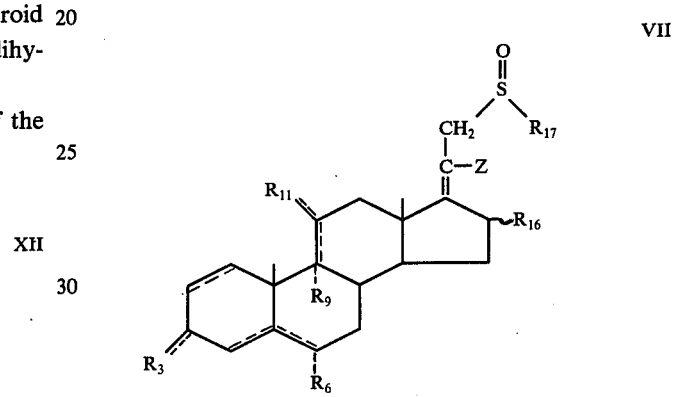

VII 3. reacting the product of step (2) with a thiophile selected from the group consisting of trimethylphosphite and diethyl amine to form a compound of the formula

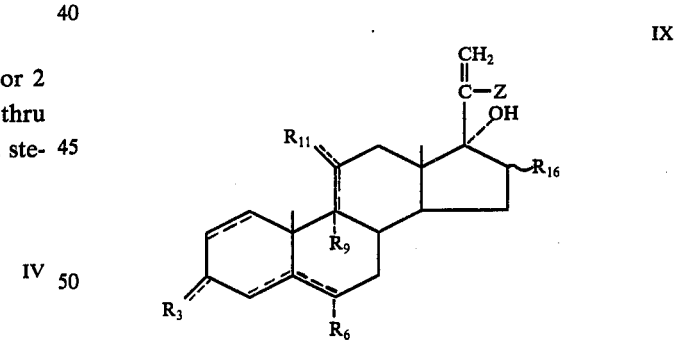

IX and 4. adding a peracid to the product of step (3), where $R_3$, $R_6$, $R_9$, $R_{11}$, $R_{16}$, $R_{17}$, $R_{20}$, $R_{120}$, $R_{121}$, $\sim$, $\rightleftharpoons$, Z and M are defined in claim 1.

9. A process according to claim 8, where the substituted sulfenylating agent is an aromatic sulfenyl chloride and where the Michael addition is with an alkoxide.

10. The process according to claim 9, where the aromatic sulfenyl chloride is phenylsulfenyl chloride or tolylsulfenyl chloride and where the alkoxide is methoxide or ethoxide.

11. The process according to claim 10, where the aromatic sulfenyl chloride is phenylsulfenyl chloride, where the alkoxide is methoxide and thiophile is trimethylphosphite.

12. A process according to claim 11 where the steroid of formula XII is beclomethansone (9α-chloro-11β,17α,21-trihydroxy-16β-methylpregna-1,4-diene-3,20-dione).

13. A process according to claim 11, where the steroid of formula XII is bethamethasone (9α-fluoro-11β,17α,21-trihydroxy-16β-methylpregna-1,4-diene-3,20-dione).

14. A process according to claim 11, where the steroid of formula XII is cortisone (17α,21-dihydroxypregna-4-ene-3,11,20-trione).

15. A process according to claim 11, where the steroid of formula XII is dexamethasone(9α-fluoro-11β,17α,21-trihydroxy-16α-methylpregna-1,4-diene-3,20-dione).

16. A process according to claim 11, where the steroid of formula XII is difluorasone (6α,9β-difluoro-11β,17α,21-trihydroxy-16β-methyl-pregna-1,4-diene-3,20-dione 17,21-diacetate).

17. A process according to claim 11, where the steroid of formula XII is fludrocortisone (9α-fluoro-11β,17α,21-trihydroxypregna-4-ene-3,20-dione).

18. A process according to claim 11, where the steroid of formula XII is flumethasone (6α,9α-difluoro-11β,17α,21-trihydroxy-16α-methyl-pregna-1,4-diene-3,20-dione).

19. A process according to claim 11, where the steroid of formula XII is fluprednisolone (6α-fluoro-11β,17α,21-trihydroxypregna-1,4-diene-3,20-dione).

20. A process according to claim, where the steroid of formula XII is hydrocortisone (11β,17α,21-tihydroxypregna-4-ene-3,20-dione).

21. A process according to claim 11, where the steroid of formula XII is meprednisone (17α,21-dihydroxy-16β-methylpregna-1,4-diene 3,11,20-trione).

22. A process according to claim 11, where the steroid offormula XII is methylprenisolone (11β,17α,21-trihydroxy-6α-methylpregna-1,4-diene-3,20-dione)

23. A process according to claim 11, where a steroid of the formula XII is paramethasone (6α-fluoro-11β,17α,21-trihydroxy-16α-methylpregna-1,4-diene-3,20-dione).

24. A process according to claim 11, where a steroid of the formula XII is prednisolone (11β,17α,21-trihydroxypregna-1,4-diene-3,20-dione).

25. A process according to claim 11, where a steroid of the formula XII is prednisone (17α,21-dihydroxypregna-1,4-diene-3,11,20-trione).

26. A process for the preparation of a steroid of the formula

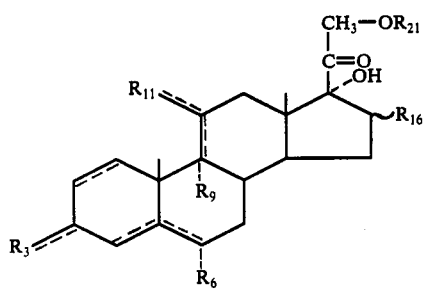

XII which comprises starting with a steroidal propargyl alcohol of the formula

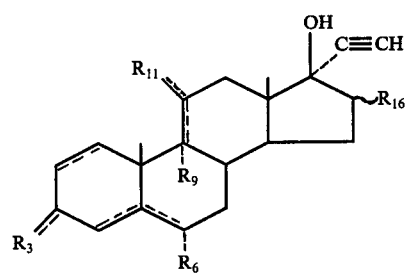

IV and subjecting the steroidal propargyl alcohol IV to the following reactions:

1. sulfenylating with a substituted sulfenylating agent of the formula $R_{17}$-S-M, to form an allene sulfoxide of the formula

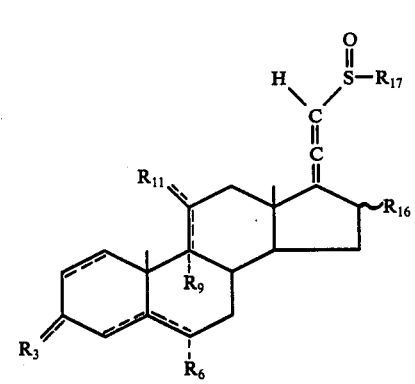

VI

2. Michael addition to the allene sulfoxide of step (1) with an alkoxide, mercaptide or dialkyl amine to form a sulfoxide of the formula

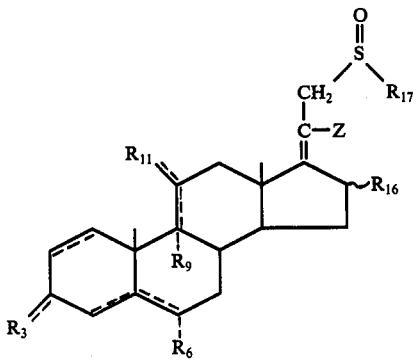

VII 3. reacting the product of step (2) with a thiophile selected from the group consisting of trimethylphosphite and diethylamine to form a compound of the formula

IX

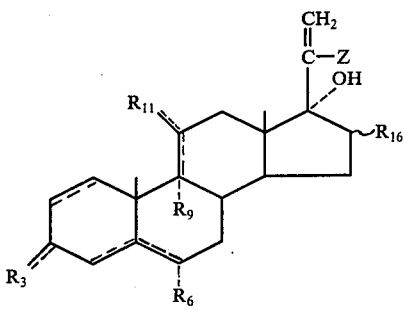

4. adding a halogen to the product of step (3) to produce a compound of the formula

XI

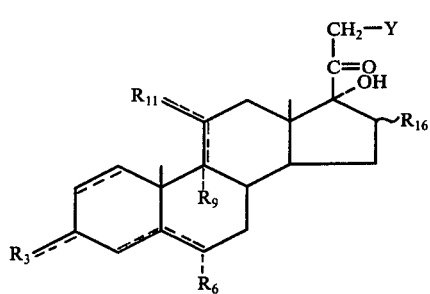

where Y is a chlorine, bromine, or iodine atom; and
5. substituting an anion of the formula $OR_{21}$ for Y in the product of step (4) where $R_3$, $R_6$, $R_9$, $R_{11}$, $R_{16}$, $R_{17}$, $R_{20}$, $R_{120}$, $R_{121}$, $\sim$, $===$, Z and M are defined in claim 1 and where $R_{21}$ is defined in claim 8.

27. A process according to claim 26, where the substituted sulfenylating agent is an aromatic sulfenyl chloride and where the Michael addition is with an alkoxide.

28. The process according to claim 27, where the aromatic sulfenyl chloride is phenylsulfenyl chloride or tolylsulfenyl chloride and where the alkoxide is methoxide or ethoxide.

29. A process according to claim 28, where the aromatic sulfenyl chloride is phenylsulfenyl chloride, where the alkoxide is methoxide and the thiophile is trimethylphosphite.

30. A process according to claim 29, where the steroid of formula XII is beclomethasone (9α-chloro-11β,17α,21-trihydroxy-16β-methylpregna-1,4-diene-3,20-dione).

31. A process according to claim 29, where the steroid of formula XII is betamethasone (9α-fluoro-11β,17α,21-trihydroxy-16β-methylpregna-1,4-diene-3,20-dione).

32. A process according to claim 29, where the steroid of formula XII is cortisone (17α,21-dihydroxypregna-4-ene-3,11,20-trione).

33. A process according to claim 29, where the steroid of formula XII is dexamethasone (9α-fluoro-11β,17α,21-trihydroxy-16α-methylpregna-1,4-diene-3,20-dione).

34. A process according to claim 29, where the steroid of formula XII is difluoroasone (6α,9α-difluoro-11β,17α,21-trihydroxy-16β-methyl-pregna-1,4-diene-3,20-dione 17,21--diacetate).

35. A process according to claim 29, where the steroid of formula XII is fludrocortisone(9α-fluoro-11β,17α,21trihydroxypregna-4-ene-3,20 -dione).

36. A process according to claim 29, where the steroid of formula XII is flumethasone (6α,9α-difluoro-11β,17α,21-trihydroxy-16α-methyl-pregna-1,4-diene-3,20 -dione).

37. A process according to claim 29, where the steroid of formula XII is fluprednisolone (6α-fluoro-11β,17α, 21-trihydroxypregna-1,4-diene-3,20-dione).

38. A process according to claim 29, where the steroid of formula XII is hydrocortisone (11β,17α,21-trihydroxypregna-4-ene-3,20-dione).

39. A process according to claim 29, where the steroid of formula XII is meprednisone (17α,21-dihydroxy-16β-methylpregna-1,4-diene 3,11,20-trione).

40. A process according to claim 29, wherein the steroid of formula XII is methylprednisolone (11β,17α,21-trihydroxy-6α-methylpregna-1,4-diene-3,20-dione).

41. A process accordingto claim 29, where the steroid of formula XII is paramethasone (6α-fluoro-11β,17α,21-trihydroxy-16α-methylpregna-1,4-diene-3.20-dione).

42. A process according to claim 29, where the steroid of formula XII is prednisolone (11β,17α,21-trihydroxypregna-1,4-diene-3,20-dione).

43. A process according to claim 29, where the steroid of formula XII is prednisone (17α,21-dihydroxypregna-1,4-diene-3,11,20-trione).

44. A process for the production of an allene sulfoxide of the formula

VI

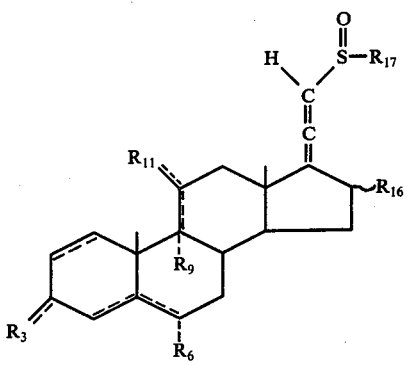

which comprises starting with a steroidal propargyl alcohol of the formula

IV

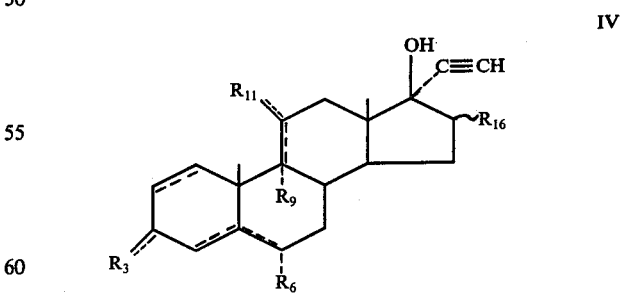

and sulfenylating the steroidal propargyl alcohol IV with a substituted sulfenylating agent of the formula $R_{17}$-S-M, where $R_3$, $R_6$, $R_9$, $R_{11}$, $R_{16}$, $R_{17}$, $R_{121}$, $\sim$, $===$ and M are defined in claim 1.

45. A process for the preparation of a sulfoxide of the formula

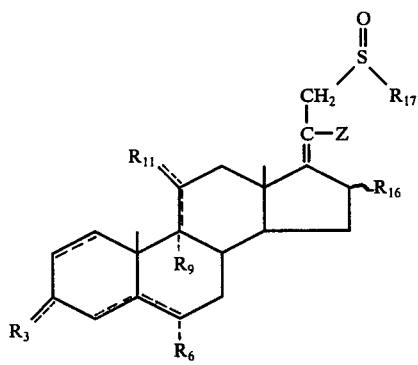
VII which comprises starting with an allene sulfoxide of the formula

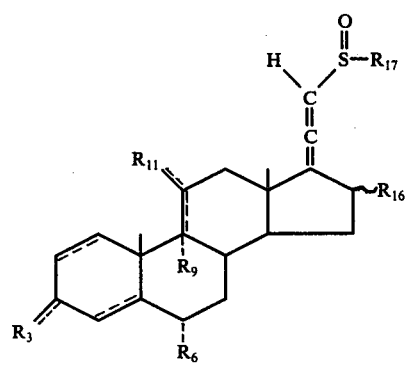
VI and subjecting the allene sulfoxide VI to Michael addition with an alkoxide, mercaptide, or dialkylamine, where $R_3$, $R_6$, $R_9$, $R_{11}$, $R_{16}$, $R_{17}$, $R_{20}$, $R_{120}$, $R_{121}$, ~, --- and Z are defined in claim 1.

46. A process for the preparation of a 17α-hydroxy steroid of the formula

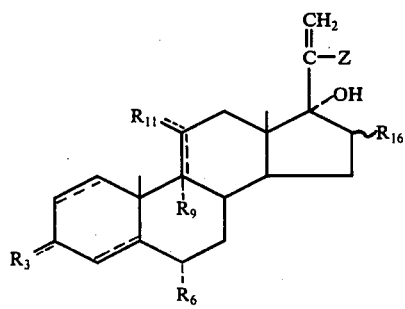
IX which comprises starting with a sulfoxide of the formula

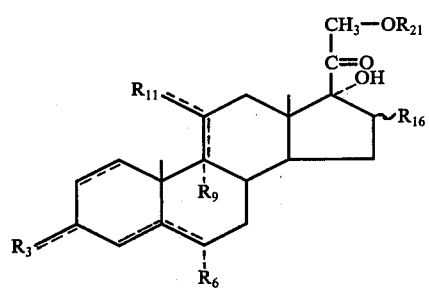
VII and reacting the formula VII compound with a thiophile selected from the group consisting of trimethylphosphite and diethylamine where $R_3$, $R_6$, $R_9$, $R_{11}$, $R_{16}$, $R_{17}$, $R_{20}$, $R_{120}$, $R_{121}$, ~, ===, and Z are defined in claim 1.

47. A process for the preparation of a steroid of the formula

XII

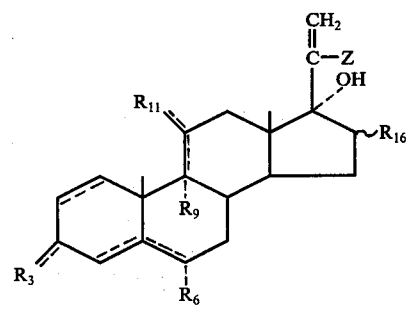

which comprises starting with a 17α-hydroxy steroid of the formula

IX and adding a peracid to compound IX, where $R_3$, $R_6$, $R_9$, $R_{11}$, $R_{16}$, $R_{20}$, $R_{120}$, ~, === and Z are defined in claim 1 and where $R_{21}$ is defined in claim 8.

48. An allene sulfoxide of the formula

VI

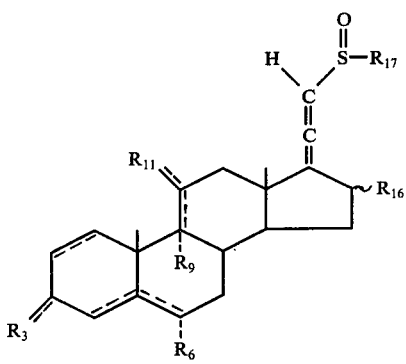

where $R_3$, $R_6$, $R_9$, $R_{11}$, $R_{16}$, $R_{17}$, $R_{121}$, ~, and ═══ are defined in claim 1.

49. 21-Phenylsulfinylpregna-4,17(20),20-triene-3-one an allene sulfoxide according to claim 48.

50. 6α-Methyl-21-phenylsulfinylpregna-4,17(20),20-triene-3-one an allene sulfoxide according to claim 48.

51. 11β-Hydroxy-21-phenylsulfinylpregna-4,17-(20),20-triene-3-one an allene sulfoxide according to claim 48.

52. 11β-Hydroxy-6α-methyl-21-phenylsulfinylpregna-4,17(20),20-triene-3-one an allene sulfoxide according to claim 48.

53. 21-Phenylsulfinylpregna-4,9-(11),17(20),20-tetraene-3-one an allene sulfoxide according to claim 48.

54. 21-Phenylsulfinylpregna-1,4,9(11),17(20),20-pentaene-3-one an allene sulfoxide according to claim 48.

55. 6α-Methyl-21-phenylsulfinylpregna-4,9(11),17(20),20-tetraene-3-one an allene sulfoxide according to claim 48.

56. 6α-Methyl-21-phenylsulfinylpregna-1,4,9(11),17(20),20-pentaene-3-one an allene sulfoxide according to claim 48.

57. 6α-Fluoro-21-phenylsulfinylpregna-4,9(11),17(20),20-tetraene-3-one an allene sulfoxide according to claim 48.

58. 6α-Fluoro-21-phenylsulfinylpregna-1,4,9(11),17(20),20-pentaene-3-one an allene sulfoxide according to claim 48.

59. 16α-Methyl-21-phenylsulfinylpregna-4,9,(11),17(20),20-tetraene-3-one an allene sulfoxide according to claim 48.

60. A sulfoxide of the formula

VII

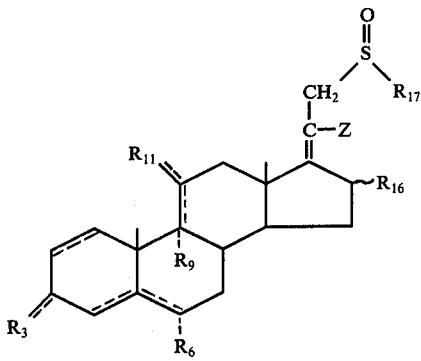

where $R_3$, $R_6$, $R_9$, $R_{11}$, $R_{16}$, $R_{17}$, $R_{20}$, $R_{120}$, $R_{121}$, ~, ═══ and Z are defined in claim 1.

61. 20-Methoxy-21-phenylsulfinylpregna-4,17-(20)-diene-3-one a sulfoxide according to claim 60.

62. 20-Methoxy-6α-methyl-21-phenylsulfinylpregna-4,17(20)-diene-3-one a sulfoxide according to claim 60.

63. 11β-Hydroxy-20-methoxy-21-phenylsulfinylpregna-4,17(20)-diene-3-one a sulfoxide according to claim 60.

64. 11β-Hydroxy-20-methoxy-6α-methyl-21-phenylsulfinyl-pregna-4,17-(20)-diene-3-one a sulfoxide according to claim 60.

65. 20-Methoxy-21-phenylsulfinylpregna-4,9-(11),17(20)-triene-3-one a sulfoxide according to claim 60.

66. 20-Methoxy-21-phenylsulfinylpregna-1,4,9(11),17(20)-tetraene-3-one a sulfoxide according to claim 60.

67. 20-Methoxy-6α-methyl-21-phenylsulfinylpregna-4,9(11),17(20)-triene-3-one a sulfoxide according to claim 60.

68. 20-Methoxy-6α-methyl-21-phenylsulfinylpregna-1,4,9-(11),17(20)-tetraene-3-one a sulfoxide according to claim 60.

69. 6α-Fluoro-20-methoxy-21-phenylsulfinylpregna-4,9(11),17(20)-triene-3-one a sulfoxide according to claim 60.

70. 6α-Fluoro-20-methoxy-21-phenylsulfinylpregna-1,4,9(11),17(20)-tetraene-3-one a sulfoxide according to claim 60.

71. 20-Methoxy-16α-methyl-21-phenylsulfinylpregna-4,9(11),17(20)-triene-3-one a sulfoxide according to claim 60.

72. A 17α-hydroxy steroid of the formula

IX

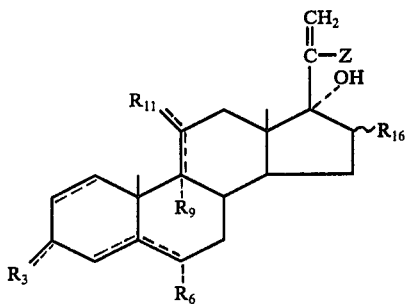

where $R_3$, $R_6$, $R_9$, $R_{11}$, $R_{16}$, $R_{120}$, ~, ═══ and Z are defined in claim 1.

73. 17α-Hydroxy-20-methoxypregna-4,20-diene-3-one a 17α-hydroxy steroid according to claim 72.

74. 17α-Hydroxy-20-methoxy-6α-methylpregna-4,20-diene-3-one a 17α-hydroxy steroid according to claim 72.

75. 11β,17α-Dihydroxy-20-methoxypregna-4,20-diene-3-one a 17α-hydroxy steroid according to claim 72.

76. 11β,17α-Dihydroxy-20-methoxy-6α-methylpregna-4,20-diene-3-one a 17α-hydroxy steroid according to claim 72.

77. 17α-Hydroxy-20-methoxypregna-4,9(11),20-triene-3-one a 17α-hydroxy steroid according to claim 72.

78. 17α-Hydroxy-20-methoxypregna-1,4,9(11),20-tetraene-3-one a 17α-hydroxy steroid according to claim 72.

79. 17α-Hydroxy-20-methoxy-6α-methylpregna-4,9(11),20-triene-3-one a 17α-hydroxy steroid according to claim 72.

80. 17α-Hydroxy-20-methoxy-6α-methylpregna-1,4,9(11),20-tetraene-3-one a 17α-hydroxy steroid according to claim 72.

81. 6α-Fluoro-17α-hydroxy-20-methoxypregna-4,9(11),20-triene-3-one a 17α-hydroxy steroid according to claim 72.

82. 6α-Fluoro-17α-hydroxy-20-methoxypregna-1,4,9(11),20-tetraene-3-one a 17α-hydroxy steroid according to claim 72.

83. 17α-Hydroxy-20-methoxy-16α-methylpregna-4,9(11),20-triene-3-one a 17α-hydroxy steroid according to claim 72.

84. 21-Bromo-17α-hydroxypregna-4,9(11)-diene-3,20-dione a 21-halo steroid.

85. 21-Bromo-17α-hydroxypregna-1,4,9(11)-triene-3,20-dione a 21-halo steroid.

86. 21-Bromo-17α-17α-hydroxy-6α-methylpregna-4,9(11)-diene-3,20-dione a 21-halo steroid.

87. 21-Bromo-17α-hydroxy-6α-methylpregna-1,4,9(11)-triene-3,20-dione a 21-halo steroid.

88. 21-Bromo-6α-fluoro-17α-hydroxypregna-4,9(11)-diene-3,20-dione a 21-halo steroid.

89. 21-Bromo-6α-fluoro-17α-hydroxypregna-1,4,9(11)-triene-3,20-dione a 21-halo steroid.

90. 21-Bromo-17α-hydroxy-16α-methylpregna-4,9(11)-diene-3,20-dione a 21-halo steroid.

91. A process according to claim 11 where the steroid of formula XII is 17α,21-dihydroxypregna-4,8(11)-diene-3,20-dione 21-acetate.

92. A process according to claim 29 where the steroid of formula XII is 17α,21-dihydroxypregna-4,9(11)-diene-3,20-dione 21-acetate.

* * * * *

UNITED STATES PATENT AND TRADEMARK OFFICE
CERTIFICATE OF CORRECTION

PATENT NO. : 4,041,055                                    Page 1 of 3
DATED      : August 9, 1977
INVENTOR(S): Kenneth P. Shephard, Verlan H. VanRheenen It is certified that error appears in the above–identified patent and that said Letters Patent are hereby corrected as shown below:

Column 1, line 29, "11" should read --II--. Column 2, line 38, "3α-hydroxy androst-" should read --3β-hydroxyandrost- --; line 39, "steriods" should read --steroids--; line 45, "steriods" should read --steroids--. Column 3, lines 20-33, formula VI should read

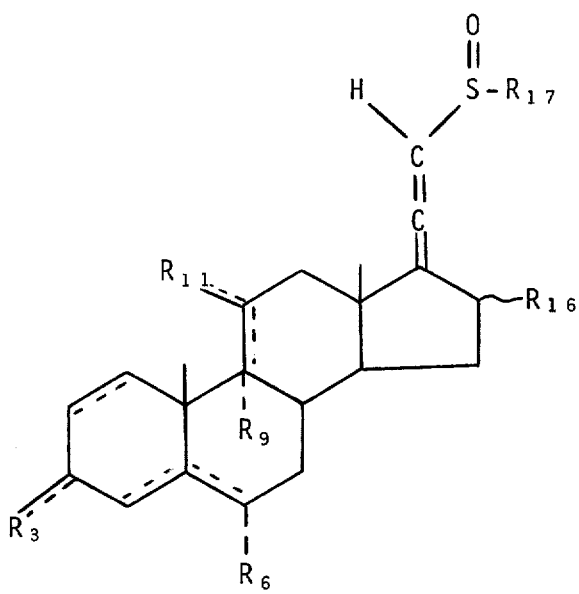

Column 3, line 34, "Micheal" should read --Michael--. Column 4, line 9, "$CH_3-OR_{21}$" should read --$CH_2-OR_{21}$--; line 27, "steriod" should read --steroid--. Column 5, line 64, "Micheal" should read --Michael--; line 65, "of" should read --or--; line 67, "steriod" should read --steroid--. Column 6, line 36, "steriod" should read --steroid--; line 36, "formula." should read --formula--; line 41, "$CH_3-OR_{21}$" should read --$CH_2-OR_{21}$--; line 52, "steriod" should

UNITED STATES PATENT AND TRADEMARK OFFICE
CERTIFICATE OF CORRECTION

PATENT NO. : 4,041,055
DATED : August 9, 1977
INVENTOR(S) : Kenneth P. Shephard, Verlan H. VanRheenen It is certified that error appears in the above-identified patent and that said Letters Patent are hereby corrected as shown below:

Page 2 of 3 read --steroid--. Column 7, line 3, "steriod" should read --steroid--; line 3, "steriod" should read --steroid--. Column 9, "Broken arrows on each side of Chart C" should be --one long arrow on each side of Chart C--. Column 10, line 30, "lll" should read --III--; line 34, "be either" should read --be in either--; line 48, "lll" should read --III--; line 49, "steriod" should read --steroid--; line 51, "LIC≡Ch" should read --LiC≡CH--; line 51, "steriod" should read --steroid--; line 55, "steriod" should read --steroid--. Column 11, line 20, "l-)2-" should read --1-(2- --; line 55, "cyclohexane" should read --cyclohexene--. Column 14, line 30, "for" should read --of--. Column 15, line 61, "β" should read --B--. Column 18, line 39, "$R_3$ is (H,H), $R_6$, $R_9$," should read --$R_3$ is (O), $R_{11}$ is (H,H), $R_6$, $R_9$,--; line 52, "of title" should read --of the title--. Column 19, line 15, "1.5=" should read --1.5%--; line 41, "XIII" should read --XII--. Column 21, line 29, "4,9)11)," should read --4,9(11),--; line 36, "3,441,559" should read --3,441,559)--. Column 24, lines 28-9, "...pregna-;b-4" should read --...pregna-4--. Column 25, line 25, "$R_3$ a" should read --$R_3$ with a--. Column 27, lines 2-3, "tolysulfenyl" should read --tolylsulfenyl--; line 17, "fluoromethonone" should read --fluorometholone--; line 31, "$CH_3$-$OR_{21}$" should read --$CH_2$-$OR_{21}$--; line 43, "$R_{21}$ a" should read --$R_{21}$ is a--; line 65, "1 sulfenylating" should read --(1) sulfenylating--. Column 29, line 2, "beclomethansone" should read --beclomethasone--; line 6, "bethamethasone" should read --betamethasone--; line 17, "6α,9β-" should read --6α,9α- --; line 32, "tihydroxy-" should read --trihydroxy- --; line 38, "offormula" should read --of formula--; line 38, "methylprenisolone" should read --methylprednisolone--; line 55, "$CH_3$-$OR_{21}$" should read --$CH_2$-$OR_{21}$--. Column 31, line 63, "difluoroasone" should read --difluorasone--; line 65, "17,21--" should read --17,21- --; line 68, "...21tri..." should read --...21-tri...--. Column 32, line 19, "accordingto" should read

UNITED STATES PATENT AND TRADEMARK OFFICE
CERTIFICATE OF CORRECTION

PATENT NO. : 4,041,055
DATED : August 9, 1977
INVENTOR(S) : Kenneth P. Shephard, Verlan H. VanRheenen It is certified that error appears in the above-identified patent and that said Letters Patent are hereby corrected as shown below:

Page 3 of 3

--according to--; line 22, "3.20" should read --3,20--. Column 34, line 31, "$CH_3-OR_{21}$" should read --$CH_2-OR_{21}$--. Column 35, line 29, "4,9-(11)," should read --4,9(11),--; line 67, "4,17-(20)-" should read --4,17(20)- --. Column 36, line 7, "4,17-(20)-" should read --4,17(20)- --; line 20, "1,4,9-(11)," should read --1,4,9(11),--. Column 38, line 12, "4,8(11)-" should read --4,9(11)- --.

Column 4, line 23, "reactionsof" should read --reactions of--. Column 10, line 34, "incicates" should read --indicates--. Column 14, line 1, "tertiay" should read --tertiary--; line 21, "propargly" should read --propargyl--; line 30, "propargly" should read --propargyl--. Column 15, line 37, "P-TSA" should read --p-TSA--. Column 17, line 2, "surfuryl" should read --sulfuryl--; line 56, "Methylethisterterone" should read --Methylethisterone--. Column 19, line 14, "CDCL$_3$" should read --CDCl$_3$--. Column 21, line 69, "tetrane" should read --tetraene--. Column 29, line 31, "claim," should read --claim 11,--.

Signed and Sealed this

Fourth Day of April 1978

[SEAL]

Attest:

RUTH C. MASON
Attesting Officer

LUTRELLE F. PARKER
Acting Commissioner of Patents and Trademarks

Disclaimer 4,041,055.—*Kenneth Paul Shephard* and *Verlan H. Van Rheenen*, Portage, Mich. PROCESS FOR THE PREPARATION OF 17α-HYDROXYPROGESTERONES AND CORTICOIDS FROM ANDROSTENES. Patent dated Aug. 9, 1977. Disclaimer filed May 22, 1978, by the assignee, *The Upjohn Company*.

Hereby enters this disclaimer to claim 84 of said patent.

[*Official Gazette July 18, 1978.*]